US009441185B2

(12) United States Patent
Amorelli et al.

(10) Patent No.: US 9,441,185 B2
(45) Date of Patent: *Sep. 13, 2016

(54) PERFUME SYSTEMS

(71) Applicant: The Procter & Gamble Company, Cincinnati, OH (US)

(72) Inventors: Benjamin Amorelli, Farmingdale, NJ (US); Michael G. Monteleone, Hazlet, NJ (US); Adam P. Closson, Jersey City, NJ (US); Anthony T. Levorse, Jr., Westfield, NJ (US); Nicole O'Keefe, Brick, NJ (US); Gary J. Mertz, Robbinsville, NJ (US); Feng Geng, Piscataway, NJ (US); Tingwei Cai, Holmdel, NJ (US); Edward Mark Arruda, Easton, PA (US); Anubhav P. S. Narula, Hazlet, NJ (US); Robert P. Belko, Monroe, NJ (US); James Anthony Lasome, Matawan, NJ (US); Heedong Yun, Tenafly, NJ (US); Richard A. Weiss, Livingston, NJ (US); Takashi Sasaki, Belford, NJ (US); Johan Smets, Lubbeek (BE); Hugo Robert Germain Denutte, Hofstade (Aalst) (BE); An Pintens, Brasschaat (BE); Isabelle Guimet, St. Gilles (BE)

(73) Assignee: The Procter & Gamble Company, Cincinnati, OH (US)

( * ) Notice: Subject to any disclaimer, the term of this patent is extended or adjusted under 35 U.S.C. 154(b) by 7 days.

This patent is subject to a terminal disclaimer.

(21) Appl. No.: 14/334,692

(22) Filed: Jul. 18, 2014

(65) Prior Publication Data

US 2014/0329733 A1 Nov. 6, 2014

Related U.S. Application Data

(63) Continuation of application No. PCT/US2013/022007, filed on Jan. 18, 2013.

(60) Provisional application No. 61/587,794, filed on Jan. 18, 2012.

(51) Int. Cl.
| | |
|---|---|
| *A61K 8/00* | (2006.01) |
| *C11B 9/00* | (2006.01) |
| *A61Q 13/00* | (2006.01) |
| *C11D 3/50* | (2006.01) |
| *A61K 8/73* | (2006.01) |
| *A61K 8/81* | (2006.01) |
| *A61K 8/84* | (2006.01) |
| *A61K 8/11* | (2006.01) |

(52) U.S. Cl.
CPC ............... *C11B 9/008* (2013.01); *A61K 8/11* (2013.01); *A61K 8/738* (2013.01); *A61K 8/8141* (2013.01); *A61K 8/84* (2013.01); *A61Q 13/00* (2013.01); *C11B 9/003* (2013.01); *C11B 9/0015* (2013.01); *C11B 9/0034* (2013.01); *C11B 9/0046* (2013.01); *C11B 9/0076* (2013.01); *C11D 3/50* (2013.01); *A61K 2800/413* (2013.01); *A61K 2800/56* (2013.01); *A61K 2800/57* (2013.01)

(58) Field of Classification Search
CPC .................................................... C11B 9/0015
USPC .......................................................... 512/13
See application file for complete search history.

(56) References Cited

U.S. PATENT DOCUMENTS

| | | | |
|---|---|---|---|
| 4,162,687 | A | 7/1979 | Lorch |
| 4,430,243 | A | 2/1984 | Bragg |
| 4,442,025 | A | 4/1984 | Boelens et al. |
| 4,524,020 | A | 6/1985 | Sprecker et al. |
| 4,627,935 | A | 12/1986 | Hall |
| 4,760,050 | A | 7/1988 | Van Der Weerdt et al. |
| 4,776,358 | A | 10/1988 | Lorch |
| 4,933,320 | A | 6/1990 | Sprecker et al. |
| 5,283,237 | A | 2/1994 | Boden et al. |
| 5,574,179 | A | 11/1996 | Wahl et al. |
| 5,576,282 | A | 11/1996 | Miracle et al. |
| 5,595,967 | A | 1/1997 | Miracle et al. |
| 5,597,936 | A | 1/1997 | Perkins et al. |
| 5,767,305 | A | 6/1998 | Monteleone et al. |
| 5,972,878 | A | 10/1999 | Sonnenberg et al. |
| 6,225,464 | B1 | 5/2001 | Hiler, II et al. |
| 6,306,812 | B1 | 10/2001 | Perkins et al. |
| 6,326,348 | B1 | 12/2001 | Vinson et al. |
| 7,281,541 | B2 | 10/2007 | Lorch |
| 8,754,028 | B2 | 6/2014 | Velazquez et al. |

(Continued)

FOREIGN PATENT DOCUMENTS

| | | |
|---|---|---|
| EP | 0053716 A1 | 6/1982 |
| EP | 0 141 266 A2 | 5/1985 |

(Continued)

OTHER PUBLICATIONS

International Search Report; International Application No. PCT/US2013/022007; date of mailing Sep. 20, 2013; 23 pages.

(Continued)

*Primary Examiner* — John Hardee
(74) *Attorney, Agent, or Firm* — James F. McBride; Steven W. Miller

(57) ABSTRACT

The present application relates to perfume delivery systems and consumer products comprising perfume delivery systems and or perfume raw materials, as well as processes for making and using such perfume delivery systems and consumer products.

14 Claims, No Drawings

(56) References Cited

U.S. PATENT DOCUMENTS

| | | |
|---|---|---|
| 2007/0275866 A1 | 11/2007 | Dykstra |
| 2008/0305977 A1 | 12/2008 | Smets et al. |
| 2010/0305021 A1 | 12/2010 | Dykstra |
| 2011/0086793 A1 | 4/2011 | Smets et al. |
| 2011/0152146 A1 | 6/2011 | Denutte et al. |
| 2012/0004326 A1 | 1/2012 | Closson et al. |

FOREIGN PATENT DOCUMENTS

| | | |
|---|---|---|
| EP | 0 376 385 A2 | 7/1990 |
| FR | 2 634 203 A1 | 1/1990 |
| WO | WO 00/32601 A2 | 6/2000 |

OTHER PUBLICATIONS

Zuolin Zhu, et al., "Aqueous Catalysis: Methylrhenium Trioxide (MTO) as a Homogeneous Catalyst for the Diels-Alder Reaction", Journal of the American Chemical Society, Apr. 1, 1997, pp. 3507-3512, vol. 119, No. 15.

Hansch and Leo, Methods of Calculating Partition Coefficients, Comprehensive Medicinal Chemistry, 1990, p. 295, vol. 4, Pergamon Press.

ASTM method D2887-04a, "Standard Test Method for Boiling Range Distribution of Petroleum Fractions by Gas Chromatography", ASTM International.

Huaxue Yanjiu Yu Yingyong, 2003, pp. 229-230, to Peng, A., Xia, M., Jin, X.

PERFUME SYSTEMS

FIELD OF INVENTION

The present application relates to perfume delivery systems and consumer products comprising such perfume delivery systems and/or perfume raw materials as defined herein, as well as processes for making and using such perfume delivery systems and consumer products.

BACKGROUND OF THE INVENTION

Consumer products may comprise one or more perfumes and/or perfume delivery systems that can mask an undesirable odor and/or provide a desired scent to a product and/or a situs that is contacted with such a product. While current perfumes and perfume delivery systems provide desirable fragrances, consumers continue to seek products that have scents that may be longer lasting and that are tailored to their individual desires (see for example USPA 2007/0275866 A1 and USPA 2008/0305977 A1)—unfortunately the pool of perfume raw materials and perfume delivery systems that is available is still too limited to completely meet the perfume community's needs. Thus, perfumers need an ever larger pool of perfume raw materials and perfume delivery systems.

Applicants believe that the perfume raw materials and perfumes, including the delivery systems, disclosed herein expand the perfume community's options, as such perfume raw materials can provide variations on character and such perfumes can provide desired odor profiles in consumer products. In certain aspects, such perfume delivery systems comprising such perfume raw materials may provide variations on character and/or odor profiles that are better than expected as measured by parameters such as headspace analysis (employed to determine perfume delivery system perfume leakage and/or perfume delivery efficiency), ClogP, boiling point and/or odor detection threshold.

SUMMARY OF THE INVENTION

The present application relates to perfume delivery systems and consumer products comprising such perfume delivery systems and/or perfume raw materials, as well as processes for making and using such perfume delivery systems and consumer products.

DETAILED DESCRIPTION OF THE INVENTION

Definitions

As used herein "consumer product" means baby care, beauty care, fabric & home care, family care, feminine care, health care, snack and/or beverage products or devices generally intended to be used or consumed in the form in which it is sold. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for and/or methods relating to treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term "cleaning and/or treatment composition" is a subset of consumer products that includes, unless otherwise indicated, beauty care, fabric & home care products. Such products include, but are not limited to, products for treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners including toilet bowl cleaners; hair shampoos and hair-rinses; shower gels, fine fragrances and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists all for consumer or/and institutional use; and/or methods relating to oral care including toothpastes, tooth gels, tooth rinses, denture adhesives, tooth whitening.

As used herein, the term "fabric and/or hard surface cleaning and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners including toilet bowl cleaners; and metal cleaners, fabric conditioning products including softening and/or freshening that may be in liquid, solid and/or dryer sheet form; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists. All of such products which were applicable may be in standard, concentrated or even highly concentrated form even to the extent that such products may in certain aspect be non-aqueous.

As used herein, articles such as "a" and "an" when used in a claim, are understood to mean one or more of what is claimed or described.

As used herein, the terms "include", "includes" and "including" are meant to be non-limiting.

As used herein, the term "solid" includes granular, powder, bar and tablet product forms.

As used herein, the term "fluid" includes liquid, gel, paste and gas product forms.

As used herein, the term "situs" includes paper products, fabrics, garments, hard surfaces, hair and skin.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Perfume Raw Materials (Herein after "PRMs")

Suitable PRMs for employment in perfume delivery systems and/or consumer products as detailed herein include the PRMs listed in Table 1 below and stereoisomers thereof.

TABLE 1

| | Chemical Structure | IUPAC Names | Character description |
|---|---|---|---|
| 1 | 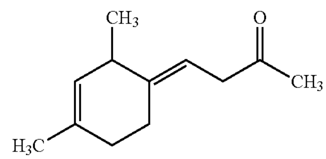 | 4-(2,4-dimethyl-cyclohex-3-enylidene)-butan-2-one | strong woody and spicy characters |
| 2 | 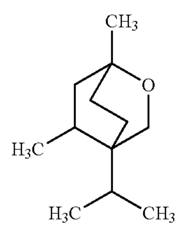 | 4-isopropyl-1,5-dimethyl-2-oxa-bicyclo[2.2.2]octane | herbal, camphor, woody, minty, and patchouli aspects |
| 3 | 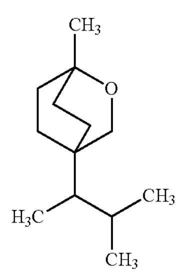 | 4-(1,2-dimethyl-propyl)-1-methyl-2-oxa-bicyclo[2.2.2]octane | anisic, green, powdery, and fruity notes |
| 4 | 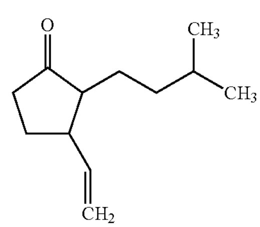 | 2-(3-methyl-butyl)-3-vinyl-cyclopentanone | lactonic, peach, buttery, floral, fruity, marigold, green, herbaceous, and minty characters |

TABLE 1-continued

| | Chemical Structure | IUPAC Names | Character description |
|---|---|---|---|
| 5 | 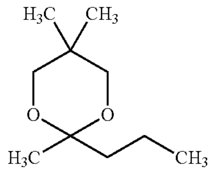 | 2,5,5-trimethyl-2-propyl-[1,3]dioxane | fruity and anise characters |
| 6 | 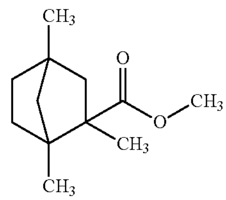 | 1,2,4-trimethyl-bicyclo[2.2.1]heptane-2-carboxylic acid methyl ester | woody, pine, camphor, herbal, and earthy characters |
| 7 | 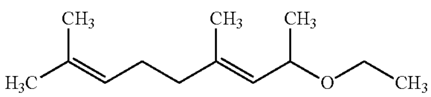 | 8-ethoxy-2,6-dimethyl-nona-2,6-diene | grapefruit, citrus, fresh, lemonile, lemonalva, and metallic characters |
| 8 | 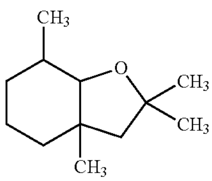 | 2,2,3a,7-tetramethyl-octahydro-benzofuran | herbal, sweet, camphor, woody, fresh, and green notes |
| 9 | 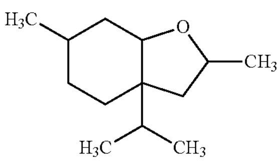 | 3a-isopropyl-2,6-dimethyl-octahydro-benzofuran | cedar wood, green, spice, flora, eucalyptus, and slight piney notes |
| 10 | 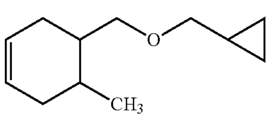 | 4-cyclopropylmethoxymethyl-5-methyl-cyclohexene | strong fruity and green characters |
| 11 | 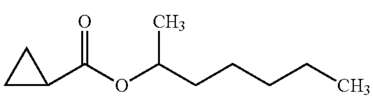 | cyclopropanecarboxylic acid 1-methyl-hexyl ester | strong fruity, herbal, seaweed, chamomile, and ambrette seed characters |
| 12 | 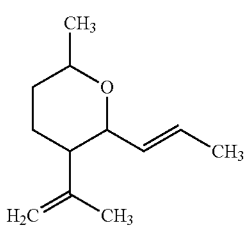 | 3-isopropenyl-6-methyl-2-propenyl-tetrahydro-pyran | strong woody, fresh, cinnamon, and spicy characters |
| 13 | 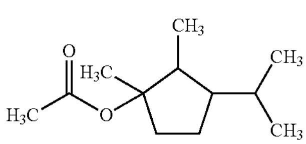 | acetic acid 3-isopropyl-1,2-dimethyl-cyclopentyl ester | strong woody, fresh, cinnamon, and spicy characters |
| 14 | 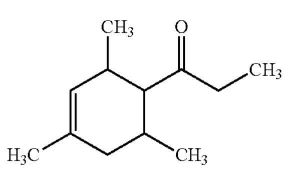 | 1-(2,4,6-trimethyl-cyclohex-3-enyl)-propan-1-one | animalic, civet, chrysanthemum leaves, and honey notes |

TABLE 1-continued

| | Chemical Structure | IUPAC Names | Character description |
|---|---|---|---|
| 16 | 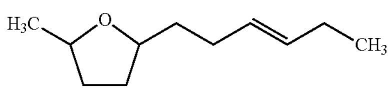 | 2-(hex-3-enyl)-5-methyl-tetrahydro-furan | strong floral and vegetable characters |
| 17 | 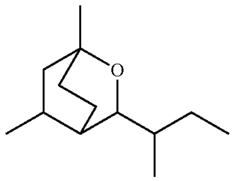 | 3-sec-Butyl-1,5-dimethyl-2-bicyclo[2.2.2]octane | sweet, warm, black-pepper, herbal |
| 18 | 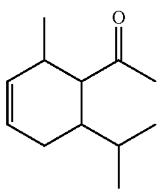 | 1-(6-Isopropyl-2-methyl-cyclohex-3-enyl)-ethanone | damascone-like, minty, rosey |
| 19 | 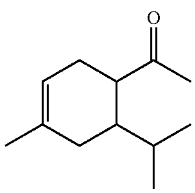 | 1-(6-Isopropyl-4-methyl-cyclohex-3-enyl)-ethanone | floral (rose), musk aspects, must spicy, slightly green |
| 20 | 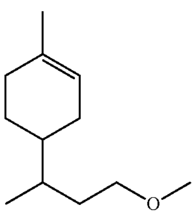 | 4-(3-Methoxy-1-methyl-propyl)-1-methyl-cyclohexene | black licorice, green, floral |
| 21 | 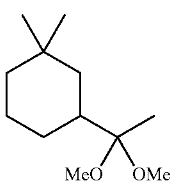 | 3-(1,1-Dimethoxy-ethyl)-1,1-dimethyl-cyclohexane | candy, herbaceous, fruity, minty |
| 22 | 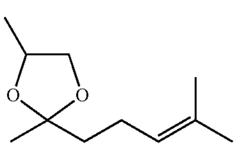 | 2,4-Dimethyl-2-(4-methyl-pent-3-nyl)-[1,3]dioxolane | floral, green, sweet, rose |

The PRMs disclosed in Table 1 above (a.k.a., molecules— as referred to in the Examples section) may provide one or more of the following benefits at levels that Applicants believe are unexpected in view of PRMs in general: neat product odor; wet fabric odor when applied to a fabric; dry fabric odor when applied to a fabric; reduced leakage from an encapsulate, including an encapsulate such as a perfume microcapsule; increased head space versus neat oil in certain perfume delivery technologies; odor when used in a matrix perfume delivery that is applied to a package; neat product odor when applied to a cleaning and/or treatment composition; fine fragrance composition odor when used in a fine fragrance; dry hair odor when a composition comprising such a PRM is applied to hair; PRM bloom from a solution comprising such a PRM; and new PRM character when applied to a situs. Confirmation of such benefits can be obtained by applying standard test methodologies detailed herein. The PRMs and stereoisomers of such PRMs disclosed in Table 1 above can be made in accordance with the teachings detailed in the present specification.

In one aspect, the PRMs disclosed in Table 1 and stereoisomers thereof are suitable for use, as defined by the present specification, in consumer products at levels, based on total consumer product weight, of from about 0.0001% to about 25%, from about 0.0005% to about 10%, from about 0.001% to about 5%, from about 0.005% to about 2.5%, or even from 0.01% to about 1%. Such PRMs and stereoisomers thereof may be used in various combinations in the aforementioned consumer products. In one aspect, a consumer product may comprise one or more PRMs selected from Table 1 Nos. 1, 2, 3, 4, 5, 6, 7, 8, 9, 10, 11, 12, 13, 14, 15, 16, 17, 18, 19, 20, 21, 22 and stereoisomers thereof.

In another aspect, the PRMs disclosed in Table 1 and stereoisomers thereof are suitable for use, as defined by the present specification, in cleaning and/or treatment compositions at levels, based on total cleaning and treatment products weight of from about 0.0001% to about 25%, from about 0.0005% to about 10%, from about 0.001% to about 5%, from about 0.005% to about 2.5%, or even from 0.01% to about 1%. Such PRMs and stereoisomers thereof may be used in various combinations in the aforementioned cleaning and/treatment compositions. In one aspect, a cleaning and/or treatment composition may comprise one or more PRMs selected from Table 1 Nos. 1, 2, 3, 4, 5, 6, 7, 8, 9, 10, 11, 12, 13, 14, 15, 16, 17, 18, 19, 20, 21, 22 and stereoisomers thereof.

In another aspect, the PRMs disclosed in Table 1 and stereoisomers thereof are suitable for use, as defined by the present specification, in fabric and/or hard surface cleaning and/or treatment compositions at levels, based on total fabric and/or hard surface cleaning and/or treatment composition weight of from about 0.00001% to about 25%, from 0.00005% to about 10%, from 0.0001% to about 5%, from 0.0005% to about 1.0%, or even from 0.001% to about 0.5%. Such PRMs and stereoisomers thereof may be used in various combinations in the aforementioned fabric and/or hard surface cleaning and/or treatment compositions. In one aspect, a fabric and/or hard surface cleaning and/or treatment composition may comprise one or more PRMs selected from Table 1 Nos. 1, 2, 3, 4, 5, 6, 7, 8, 9, 10, 11, 12, 13, 14, 15, 16, 17, 18, 19, 20, 21, 22 and stereoisomers thereof.

In another aspect, a detergent that may comprise the same level of the PRMs as disclosed for the aforementioned fabric and hard surface cleaning and/or treatment compositions is disclosed. In one aspect, a detergent may comprise one or more PRMs selected from Table 1 Nos. 1, 2, 3, 4, 5, 6, 7, 8, 9, 10, 11, 12, 13, 14, 15, 16, 17, 18, 19, 20, 21, 22 and stereoisomers thereof.

In another aspect, the PRMs disclosed in Table 1 and stereoisomers thereof are suitable for use in highly compacted consumer products, including highly compacted fabric and hard surface cleaning and/or treatment compositions. For example, the PRMs disclosed in Table 1 and stereoisomers thereof may be employed in solid or fluid highly compacted detergents at levels of from about 0.00001% to about 25%, from 0.00005% to about 10%, from 0.0001% to about 5%, from 0.0005% to about 1.0%, or even from 0.001% to about 0.5%, based on total composition weight. Such PRMs and stereoisomers thereof may be used in various combinations in the aforementioned highly compacted detergent compositions. Such highly compact detergents typically comprise a higher than normal percentage of active ingredients. In one aspect, a highly compacted detergent may comprise one or more PRMs selected from Table 1 Nos. 1-94 and stereoisomers thereof. More specifically, a highly compacted detergent may comprise one or more PRMs selected from Table 1 Nos. 1, 2, 3, 4, 5, 6, 7, 8, 9, 10, 11, 12, 13, 14, 15, 16, 17, 18, 19, 20, 21, 22 and stereoisomers thereof.

Perfume Delivery Systems

The perfume raw materials and perfume compositions disclosed herein may further be incorporated into a perfume delivery system. Suitable perfume delivery systems, methods of making perfume delivery systems and the uses of perfume delivery systems are disclosed in USPA 2007/0275866 A1. Such perfume delivery systems include:

I. Polymer Assisted Delivery (PAD):

This perfume delivery technology uses polymeric materials to deliver perfume materials. Examples of PAD include employment of classical coacervation, water soluble or partly soluble to insoluble charged or neutral polymers, liquid crystals, hot melts, hydrogels, perfumed plastics, microcapsules, nano- and micro-latexes, polymeric film formers, and polymeric absorbents, etc. Further, PAD includes, but is not limited to:

a.) Matrix Systems: The perfume is dissolved or dispersed in a polymer matrix or particle. Perfume materials may be 1) dispersed into the polymer prior to formulating into the product or 2) added separately from the polymer during or after formulation of the product. Suitable organic latex particles include a wide range of materials including, but not limited to, polyacetal, polyacrylate, polyamide, polybutadiene, polychloroprene, polyethylene, polycyclohexylene polycarbonate, polyhydroxyalkanoate, polyketone, polyester, polyetherimide, polyethersulfone, polyethylenechlorinates, polyimide, polyisoprene, polylactic acid, polyphenylene, polyphenylene, polypropylene, polystyrene, polysulfone, polyvinyl acetate, polyvinyl chloride, as well as polymers or copolymers based on amine, acrylonitrile-butadiene, cellulose acetate, ethylene-vinyl acetate, ethylene vinyl alcohol, styrene-butadiene, vinyl acetate-ethylene, and mixtures thereof. All such matrix systems may include, for example, polysaccharides and nanolatexes that may be combined with other perfume delivery technologies, including other PAD systems such as PAD reservoir systems in the form of a perfume microcapsule (PMC). Silicone-assisted delivery (SAD) may also be used. Examples of silicones include polydimethylsiloxane and polyalkyldimethylsiloxanes. Other examples include those with amine functionality, which may be used to provide benefits associated with amine-assisted delivery (AAD) and/or polymer-assisted delivery (PAD) and/or amine-reaction products (ARP).

b.) Reservoir Systems: Reservoir systems are also known as core-shell systems (e.g., perfume microcapsules). In such a system, the benefit agent is surrounded by a benefit agent release controlling membrane, which may serve as a protective shell. Suitable shell materials include reaction products of one or more amines with one or more aldehydes, such as urea cross-linked with formaldehyde or gluteraldehyde, melamine cross-linked with formaldehyde, gelatin-polyphosphate coacervates optionally cross-linked with gluteraldehyde, gelatin-gum arabic coacervates, cross-linked silicone fluids, polyamine reacted with polyisocyanates, polyamines reacted with epoxides, polyvinyl alcohol cross linked with gluteraldehyde, polydivinyl chloride, polyesters, polyamides, polyacrylates and mixtures thereof. In one aspect, said polyacrylate based materials may comprise polyacrylate formed from methylmethacrylate/dimethylaminomethyl methacrylate, polyacrylate formed from amine acrylate and/or methacrylate and strong acid, polyacrylate formed from carboxylic acid acrylate and/or methacrylate monomer and strong base, polyacrylate formed from an amine acrylate and/or methacrylate monomer and a carboxylic acid acrylate and/or carboxylic acid methacrylate monomer, and mixtures thereof.

Suitable core materials include perfume compositions, perfume raw materials, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, odor-controlling materials, chelating agents, antistatic agents, softening agents, insect and moth repelling agents, colorants, antioxidants, chelants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers and anti-foaming agents, UV protection agents for fabrics and skin, sun fade inhibitors, anti-allergenic agents, enzymes, water proofing agents, fabric comfort agents, shrinkage resistance agents, stretch resistance agents, stretch recovery agents, skin care agents, glycerin, and natural actives such as aloe vera, vitamin E, shea butter, cocoa butter, and the like, brighteners, antibacterial actives, antiperspirant actives, cationic polymers, dyes and mixtures thereof. Suitable perfume compositions may comprise enduring perfumes, such as perfume raw materials that have a cLogP greater than about 2.5 and a boiling point greater than about 250° C. Further, suitable perfume compositions may comprise blooming perfumes that comprise perfume raw materials that have a cLogP of greater than about 3 and a boiling point of less than about 260° C.

Suitable core materials can be stabilized and/or emulsified in solvent systems with organic or inorganic materials (organic materials can be polymers of anionic nature, non-ionic nature or cationic nature, like polyacrylates and polyvinyl alcohol). Suitable processes to make core-shell systems include coating, extrusion, spray drying, interfacial polymerization, polycondensation, simple coacervation, complex coacervation, free radical polymerization, in situ emulsion polymerization, matrix polymerization and combinations thereof.

Suitable characteristics for the core-shell systems include:
a) a shell thickness of from about 20 nm to about 500 nm, from about 40 nm to about 250 nm, or from about 60 nm to about 150 nm;
b) a shell core ratio of from about 5:95 to about 50:50, from about 10:90 to about 30:70, or from about 10:90 to about 15:85;
c) a fracture strength of from about 0.1 MPa to about 16 MPa, from about 0.5 MPa to about 8 MPa, or even from about 1 MPa to about 3 MPa; and
d) an average particle size of from about 1 micron to about 100 microns, from about 5 microns to about 80 microns, or even from about 15 microns to about 50 microns.

Suitable deposition and/or retention enhancing coatings that may be applied to the core-shell systems include non-ionic polymers, anionic polymers, cationic polymers such as polysaccharides including, but not limited to, cationically modified starch, cationically modified guar, polysiloxanes, poly diallyl dimethyl ammonium halides, copolymers of poly diallyl dimethyl ammonium chloride and vinyl pyrrolidone, acrylamides, imidazoles, imidazolinium halides, imidazolium halides, poly vinyl amine, copolymers of poly vinyl amine and N-vinyl formamide and mixtures thereof. In another aspect, suitable coatings may be selected from the group consisting of polyvinylformaldehyde, partially hydroxylated polyvinylformaldehyde, polyvinylamine, polyethyleneimine, ethoxylated polyethyleneimine, polyvinylalcohol, polyacrylates and combinations thereof.

Suitable methods of physically reducing and/or removing any residual type materials from the core-shell making process may be employed, such as centrifugation. Suitable methods of chemically reducing any residual type materials may also be employed, such as the employment of scavengers, for example formaldehyde scavengers including sodium bisulfite, urea, ethylene urea, cysteine, cysteamine, lysine, glycine, serine, carnosine, histidine, glutathione, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, sorbitol, glucose, cellulose, poly(vinyl alcohol), partially hydrolyzed poly(vinylformamide), poly(vinyl amine), poly(ethylene imine), poly(oxyalkyleneamine), poly(vinyl alcohol)-co-poly(vinyl amine), poly(4-aminostyrene), poly (l-lysine), chitosan, hexane diol, ethylenediamine-N,N'-bisacetoacetamide, N-(2-ethylhexyl)acetoacetamide, 2-benzoylacetoacetamide, N-(3-phenylpropyl)acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, triethylenetetramine, ammonium hydroxide, benzylamine, hydroxycitronellol, cyclohexanone, 2-butanone, pentane dione, dehydroacetic acid, or mixtures thereof.

II. Molecule-Assisted Delivery (MAD):

Non-polymer materials or molecules may also serve to improve the delivery of perfume as perfume may non-covalently interact with organic materials, resulting in altered deposition and/or release. Non-limiting examples of such organic materials include, but are not limited to, hydrophobic materials such as organic oils, waxes, mineral oils, petrolatum, fatty acids or esters, sugars, surfactants, liposomes and even other perfume raw material (perfume oils), as well as natural oils, including body and/or other soils.

III. Fiber-Assisted Delivery (FAD):

The choice or use of a situs itself may serve to improve the delivery of perfume. In fact, the situs itself may be a perfume delivery technology. For example, different fabric types such as cotton or polyester will have different properties with respect to ability to attract and/or retain and/or release perfume. The amount of perfume deposited on or in fibers may be altered by the choice of fiber, and also by the history or treatment of the fiber, as well as by any fiber coatings or treatments. Fibers may be pre-loaded with a perfume, and then added to a product that may or may not contain free perfume and/or one or more perfume delivery technologies.

IV. Amine Assisted Delivery (AAD):

The amine-assisted delivery technology approach utilizes materials that contain an amine group to increase perfume deposition or modify perfume release during product use. There is no requirement in this approach to pre-complex or pre-react the perfume raw material(s) and the amine prior to addition to the product. In one aspect, amine-containing AAD materials suitable for use herein may be non-aromatic, for example, polyalkylimine, such as polyethyleneimine (PEI), or polyvinylamine (PVAm); or aromatic, for example, anthranilates. Such materials may also be polymeric or non-polymeric. In one aspect, such materials contain at least one primary amine. In another aspect, a material that contains a heteroatom other than nitrogen, for example sulfur, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols.

V. Cyclodextrin Delivery System (CD):

This technology approach uses a cyclic oligosaccharide or cyclodextrin to improve the delivery of perfume. Typically, a perfume and cyclodextrin (CD) complex is formed. Such complexes may be preformed, formed in-situ, or formed on or in the situs.

VI. Starch Encapsulated Accord (SEA):

SEA's are starch encapsulated perfume materials. Suitable starches include modified starches such as hydrolyzed starch, acid thinned starch, starch having hydrophobic groups, such as starch esters of long chain hydrocarbons ($C_5$ or greater), starch acetates, starch octenyl succinate and mixtures thereof. In one aspect, starch esters, such as starch octenyl succinates, are employed. Suitable perfumes for encapsulation include the HIA perfumes, including those having a boiling point determined at the normal standard pressure of about 760 mmHg of 275° C. or lower, an octanol/water partition coefficient P of about 2000 or higher and an odor detection threshold of less than or equal 50 parts per billion (ppb). In one aspect, the perfume may have logP of 2 or higher.

VII. Inorganic Carrier Delivery System (ZIC):

This technology relates to the use of porous zeolites or other inorganic materials to deliver perfumes. Perfume-loaded zeolite may be used with or without adjunct ingredients used for example to coat the perfume-loaded zeolite (PLZ) to change its perfume release properties during product storage or during use or from the dry situs. Another example of a suitable inorganic carrier includes inorganic tubules, where the perfume or other active material is contained within the lumen of the nano- or micro-tubules. Monomeric and/or polymeric materials, including starch encapsulation, may be used to coat, plug, cap, or otherwise encapsulate the PLZ.

VIII. Pro-Perfume (PP):

This technology refers to perfume technologies that result from the reaction of perfume materials with other substrates or chemicals to form materials that have a covalent bond between one or more PRMs and one or more carriers. The PRM is converted into a new material called a pro-PRM (i.e., pro-perfume), which then may release the original PRM upon exposure to a trigger such as water or light. Non-limiting examples of pro-perfumes include Michael adducts (e.g., beta-amino ketones), aromatic or non-aromatic imines (Schiffs Bases), oxazolidines, beta-keto esters, and orthoesters. Another aspect includes compounds comprising one or more beta-oxy or beta-thio carbonyl moieties capable of releasing a PRM, for example, an alpha, beta-unsaturated ketone, aldehyde or carboxylic ester.

a.) Amine Reaction Product (ARP): For purposes of the present application, ARP is a subclass or species of PP. One may also use "reactive" polymeric amines in which the amine functionality is pre-reacted with one or more PRMs, typically PRMs that contain a ketone moiety and/or an aldehyde moiety, to form the ARP. Typically, the reactive amines are primary and/or secondary amines, and may be part of a polymer or a monomer (non-polymer). Such ARPs may also be mixed with additional PRMs to provide benefits of polymer-assisted delivery and/or amine-assisted delivery. Non-limiting examples of polymeric amines include polymers based on polyalkylimines, such as polyethyleneimine (PEI), or polyvinylamine (PVAm). Non-limiting examples of monomeric (non-polymeric) amines include hydroxyl amines, such as 2-aminoethanol and its alkyl substituted derivatives, and aromatic amines such as anthranilates. The ARPs may be premixed with perfume or added separately in leave-on or rinse-off applications. In another aspect, a material that contains a heteroatom other than nitrogen, for example oxygen, sulfur, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols.

In one aspect, the PRMs disclosed in Table 1 and stereoisomers thereof are suitable for use in perfume delivery systems at levels, based on total perfume delivery system weight, of from 0.001% to about 50%, from 0.005% to 30%, from 0.01% to about 10%, from 0.025% to about 5%, or even from 0.025% to about 1%.

In another aspect, the perfume delivery systems disclosed herein are suitable for use in consumer products, cleaning and treatment compositions, fabric and hard surface cleaning and/or treatment compositions, detergents, and highly compacted consumer products, including highly compacted fabric and hard surface cleaning and/or treatment compositions (e.g., solid or fluid highly compacted detergents) at levels, based on total consumer product weight, from about 0.001% to about 20%, from about 0.01% to about 10%, from about 0.05% to about 5%, from about 0.1% to about 0.5%.

In another aspect, the amount of PRMs from Table 1 present in the perfume delivery systems, based on the total microcapsule and/or nanocapsule (Polymer Assisted Delivery (PAD) Reservoir System) weight, may be from about 0.1% to about 99%, from 25% to about 95%, from 30 to about 90%, from 45% to about 90%, or from 65% to about 90%. In one aspect, microcapsules and/or nanocapsules may comprise one or more PRMs, and stereoisomers thereof, selected from Table 1 Nos. 1, 2, 3, 4, 5, 6, 7, 8, 9, 10, 11, 12, 13, 14, 15, 16, 17, 18, 19, 20, 21, 22 and mixtures thereof. In another aspect, microcapsules and/or nanocapsules may comprise one or more PRMs, and stereoisomers thereof, selected from Table 1 Nos. 1, 2, 3, 4, 7, 8, 9, 10, 11, 12, 13, 14, 15, 16, 17, 18, 19, 20, 22 and mixtures thereof.

In one aspect, the amount of total perfume based on total weight of starch encapsulates and starch agglomerates (Starch Encapsulated Accord (SEA)) ranges from 0.1% to about 99%, from 25% to about 95%, from 30 to about 90%, from 45% to about 90%, from 65% to about 90%. In one aspect, the PRMs disclosed in Table 1 and stereoisomers thereof are suitable for use in such starch encapsulates and starch agglomerates. Such PRMs and stereoisomers thereof may be used in combination in such starch encapsulates and starch agglomerates.

In another aspect, the amount of total perfume based on total weight of [cyclodextrin-perfume] complexes (Cyclodextrin (CD)) ranges from 0.1% to about 99%, from 2.5% to about 75%, from 5% to about 60%, from 5% to about 50%, from 5% to about 25%. In one aspect, the PRMs disclosed in Table 1 and stereoisomers thereof are suitable for use in such [cyclodextrin-perfume] complexes. Such PRMs and stereoisomers thereof may be used in combination in such [cyclodextrin-perfume] complexes.

In another aspect, the amount of total perfume based on total weight of Polymer Assisted Delivery (PAD) Matrix Systems (including Silicones) ranges from 0.1% to about 99%, from 2.5% to about 75%, from 5% to about 60%, from 5% to about 50%, from 5% to about 25%. In one aspect, the amount of total perfume based on total weight of a hot melt perfume delivery system/perfume loaded plastic Matrix System and ranges from 1% to about 99%, from 2.5% to about 75%, from 5% to about 60%, from 5% to about 50%, from 10% to about 50%. In one aspect, the PRMs disclosed in Table 1 and stereoisomers thereof are suitable for use in such Polymer Assisted Delivery (PAD) Matrix Systems, including hot melt perfume delivery system/perfume loaded plastic Matrix Systems. Such PRMs and stereoisomers thereof may be used in various combinations in such Polymer Assisted Delivery (PAD) Matrix Systems (including hot melt perfume delivery system/perfume loaded plastic Matrix Systems).

In one aspect, the amount of total perfume based on total weight of Amine Assisted Delivery (AAD) (including Aminosilicones) ranges from 1% to about 99%, from 2.5% to about 75%, from 5% to about 60%, from 5% to about 50%, from 5% to about 25%. In one aspect, the PRMs disclosed in Table 1 and stereoisomers thereof are suitable for use in such Amine Assisted Delivery (AAD) systems. Such PRMs and stereoisomers thereof may be used in various combinations in such Amine Assisted Delivery (AAD) systems. In one aspect, an Amine Assisted Delivery (AAD) system may comprise one or more PRMs, and stereoisomers thereof, selected from Table 1 Nos. 1, 2, 3, 4, 5, 6, 7, 8, 9, 10, 11, 12, 13, 14, 15, 16, 17, 18, 19, 20, 21, 22 and mixtures thereof.

In one aspect, the amount of total perfume based on total weight of Amine Reaction Product (ARP) ranges from 1% to about 99%, from 2.5% to about 75%, from 5% to about 60%, from 5% to about 50%, from 5% to about 25%. In one aspect, the PRMs disclosed in Table 1 and stereoisomers thereof are suitable for use in such Amine Reaction Product (ARP) systems. Such PRMs and stereoisomers thereof may be used in various combinations in such Amine Reaction Product (ARP) systems. In one aspect, an Amine Reaction Product (ARP) system may comprise one or more PRMs, and stereoisomers thereof, selected from Table 1 Nos. 1, 2, 3, 4, 5, 6, 7, 8, 9, 10, 11, 12, 13, 14, 15, 16, 17, 18, 19, 20, 21, 22 and mixtures thereof. In another aspect, an Amine Reaction Product (ARP) system may comprise one or more PRMs, and stereoisomers thereof, selected from Table 1 Nos. 2, 5, 6, 21 and mixtures thereof.

The perfume delivery technologies (a.k.a., perfume delivery systems) that are disclosed in the present specification may be used in any combination in any type of consumer product, cleaning and/or treatment composition, fabric and hard surface cleaning and/or treatment composition, detergent, and/or highly compact detergent.

Perfumes

The PRMs disclosed in Table 1 may be used to formulate perfumes. Such perfumes are combinations of PRMs that may comprise a combination of Table 1 PRMs, or one or more Table 1 PRMs and one or more additional PRMs. When used in a perfume, the Table 1 PRMs may be employed, based on total perfume weight, at levels of from about 0.01% to about 50%, from about 0.1% to about 15%, from about 0.1% to about 10% or even from about 0.5% to about 10%. Such perfumes may be utilized in various applications, including being applied neat to a situs or used in a consumer product, cleaning and/or treatment composition, fabric and hard surface cleaning and/or treatment composition, detergent, and/or a highly compact detergent.

Adjunct Materials

For the purposes of the present invention, the non-limiting list of adjuncts illustrated hereinafter are suitable for use in the compositions detailed herein (e.g., consumer products, cleaning and/or treatment compositions, fabric and hard surface cleaning and/or treatment compositions, detergents, and/or a highly compact detergents). Such adjunct materials may be desirably incorporated in certain embodiments of the compositions, for example to assist or enhance performance of the composition, for treatment of the substrate to be cleaned, or to modify the aesthetics of the composition as is the case with perfumes, colorants, dyes or the like. It is understood that such adjuncts are in addition to the components that are supplied via Applicants' perfumes and/or perfume systems detailed herein. The precise nature of these additional components, and levels of incorporation thereof, will depend on the physical form of the composition and the nature of the operation for which it is to be used.

Suitable adjunct materials include, but are not limited to, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1.

Each adjunct ingredient is not essential to Applicants' compositions. Thus, certain embodiments of Applicants' compositions may not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments. However, when one or more adjuncts are present, such adjuncts may be present as detailed below:

Surfactants—

The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—

The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—

The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—

The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—

The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—

The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—

Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—

Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282. Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand-abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor. Suitable transition-metals in the instant transition-metal bleach catalyst include manganese, iron and chromium. Suitable MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in WO 00/32601, and U.S. Pat. No. 6,225,464.

Methods of Use

Some of the consumer products disclosed herein can be used to clean or treat a situs inter alia a surface or fabric. Typically at least a portion of the situs is contacted with an embodiment of Applicants' composition, in neat form or diluted in a liquor, for example, a wash liquor and then the situs may be optionally washed and/or rinsed. In one aspect, a situs is optionally washed and/or rinsed, contacted with a particle according to the present invention or composition comprising said particle and then optionally washed and/or rinsed. For purposes of the present invention, washing includes but is not limited to, scrubbing, and mechanical agitation. The fabric may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

Test Methods

It is understood that the test methods that are disclosed in the Test Methods Section of the present application should be used to determine the respective values of the parameters of Applicants' invention as such invention is described and claimed herein.

(1) ClogP

The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor, and C. A. Ramsden, Eds. P. 295, Pergamon Press, 1990, incorporated herein by reference). ClogP values may be calculated by using the "CLOGP" program available from Daylight Chemical Information Systems Inc. of Irvine, Calif. U.S.A.

(2) Boiling Point

Boiling point is measured by ASTM method D2887-04a, "Standard Test Method for Boiling Range Distribution of Petroleum Fractions by Gas Chromatography," ASTM International.

(3) Headspace Ratio
(a) Obtain a fragrance free consumer product formulation (shampoo or leave-on conditioner).
(b) Obtain fragrance microcapsules whose water content has been adjusted to achieve a perfume content of 25 wt % in the aqueous slurry.
(c) Prepare Sample A by adding 2.0 grams of the fragrance microcapsule aqueous slurry to 95 grams of the fragrance free consumer product formulation. Then add 3.0 grams of deionized water to balance the formulation to 100 grams. Age this formulation for 1 week at 40 degrees Centigrade.
(d) Prepare Sample B by adding 0.50 grams of the neat fragrance to 95 grams of fragrance free consumer product formulation. Then add 4.5 grams of deionized water to balance the formulation to 100 grams. Age this formulation for 1 week at 40 degrees Centigrade.

The Headspace Ratio for determining perfume leakage from a perfume delivery system is defined as the headspace concentration of Sample A divided by the headspace concentration of Sample B, $$\frac{H_{Sample\_A}}{H_{Sample\_B}},$$

where $H_{Sample\_A}$ is the headspace concentration of a consumer product formulation Sample A, and $H_{Sample\_B}$ is the headspace concentration of a consumer product formulation Sample B.

The Headspace Ratio for determining perfume delivery efficiency from a perfume delivery system is defined as the headspace concentration of Sample B divided by the headspace concentration of Sample A, $$\frac{H_{Sample\_B}}{H_{Sample\_A}},$$

where $H_{Sample\_A}$ is the headspace concentration of a consumer product formulation Sample A, and $H_{Sample\_B}$ is the headspace concentration of a consumer product formulation Sample B.

Solid-Phase Micro-Extraction (SPME)-Gas Chromatography/Mass Spectrometry is used to measure the level of perfume raw materials in the headspace of products. 1.0 grams of the 1 week at 40 degrees Centigrade aged sample (shampoo or conditioner) are placed into a clean 20 ml headspace vial and allowed to equilibrate for at least 2 hours at room temperature.

The samples are then analyzed using the MPS2-SMPE-GC-MS analysis system (GC-02001-0153, MSD-02001-0154, MPS2-02001-0155).

Apparatus:
1. 20 ml headspace vial
2. Timer.
3. Gas Chromatograph (GC): Agilent model 6890 with a CIS-4 injector (Gerstel, Mulheim, Germany) and MPS-2 Autosampler and TDU. For SPME analysis, we used the split/splitless injector (not the CIS-4 injector).
4. GC column: J&W DB-5 MS, 30 M×0.25 mm ID, 1.0 m film thickness obtained from J&W Scientific of Folsom, Calif., USA.
5. Carrier gas, helium, 1.5 ml/min. flow rate.
6. The injector liner is a special SPME liner (0.75 mm ID) from Supelco.
7. The Detector is a model 5973 Mass Selective Detector obtained from Agilent Technologies, Inc., Wilmington, Del., USA having a source temperature of about 230° C., and a MS Quad temperature of about 150° C.

Analysis Procedure:
1. Transfer sample to proper sample tray and proceed with SPME-GC-MS analysis.
2. Start sequence of sample loading and analysis. In this step, the sample is allowed to equilibrate for at least two hours on the auto sampler tray, then sampled directly from the tray. The SPME fiber assembly is DVB/CAR/PDMS (50/30 um, 24 ga, 1 cm length). Sampling time is 5 minutes.
3. Injector temperature is at 260 C.
4. Then GC-MS analysis run is started. Desportion time is 5 minutes.
5. The following temperature program is used:
   i) an initial temperature of about 50° C. which is held for 3 minutes,
   ii) increase the initial temperature at a rate of about 6° C./min until a temperature of about 250° C. is reached, then 25° C./min to 275° C., hold at about 275° C. for 4.67 minute.
6. Perfume compounds are identified using the MS spectral libraries of John Wiley & Sons and the National Institute of Standards and Technology (NIST), purchased and licensed through Hewlett Packard.
7. Chromatographic peaks for specific ions are integrated using the Chemstation software obtained from Agilent Technologies, Inc., Wilmington, Del., USA.
8. The ratio for each PRM is calculated by dividing the peak area for the perfume raw material in Sample A by the peak area in Sample B.
9. Each ratio is then weighted by that perfume raw material's weight composition in the perfume.
10. The Headspace Ratio is calculated as the sum of the individual perfume raw material ratios obtained in step 9.

(4) Perfume Leakage can Also be Evaluated Via % Liquid-Liquid Extraction and Gas Chromatographic-Mass Spectrometric Analysis When determining the % perfume leakage from Perfume Microcapsules in liquid detergent, a fresh sample of liquid detergent with equal level of free perfume (without Perfume Microcapsules) must also be analyzed in parallel for reference.

1. Preparation of an Internal Standard Solution
   Stock solution of tonalid: Weigh 70 mg tonalid and add 20 ml hexane p.a.
   Internal Standard Solution solution: Dilute 200 µl of stock solution in 20 ml hexane p.a.
   Mix to homogenize
2. Perfume Extraction from Liquid Detergent without Perfume Microcapsules (Reference)
   Weigh 2 g of liquid detergent product into an extraction vessel
   Add 2 ml of Internal Standard Solution and close vessel
   Extract perfume by gently turning the extraction vessel upside-down for 20 times (manually)
   Add spoon tip of Sodium Sulphate
   After separation of layers, immediately transfer hexane-layer into Gas Chromatograph auto sampler-vial and cap vial
   Inject splitless (1.5 µl) into Gas Chromatograph injection-port
   Run Gas Chromatographic-Mass Spectrometric analysis 3. Perfume Extraction from Liquid Detergent with Perfume Microcapsules
  Weigh 2 g of liquid detergent product into an extraction vessel
  Add 2 ml of Internal Standard Solution and close vessel
  Extract perfume by gently turning the extraction vessel upside-down for 20 times (manually)
  Add spoon tip of Sodium Sulphate
  After separation of layers, immediately transfer hexane-layer into Gas Chromatograph auto sampler-vial and cap vial
  Inject splitless (1.5 µl) into Gas Chromatograph injection-port
  Run Gas Chromatographic-Mass Spectrometric analysis
4. Calculation
  The perfume leakage from capsules per individual Perfume Raw Material:

% perfume leakage=((Area Perfume Raw Material caps×Area Internal Standard Solution ref×Weight ref)/(Area Internal Standard Solution caps×Area Perfume Raw Material ref×Weight caps))×100

(5) Odor Detection Threshold (ODT)

Determined using a gas chromatograph. The gas chromatograph is calibrated to determine the exact volume of material injected by the syringe, the precise split ratio, and the hydrocarbon response using a hydrocarbon standard of known concentration and chain length distribution. The air flow rate is accurately measured and, assuming the duration of human inhalation to last 12 seconds, the sampled volume is calculated. Since the precise concentration at the detector at any point in time is known, the mass per volume inhaled is known, and hence the concentration of material.

For example, to determine whether a material has a threshold below 50 parts per bullion, solutions are delivered to the sniff port at the calculated concentration. A panelist sniffs the GC effluent and identifies the retention time when odor is noticed. The average among 6 panelists determines the threshold of noticeability. The necessary amount of analyte is injected into the column to achieve a 50 parts per billion concentration at the detector. Typical gas chromatograph parameters for determining odor detection thresholds are listed below:

GC: 5890 Series II with FID detector, 7673 Autosampler
Column: J&W Scientific DB-1
Length: 30 meters, 0.25 millmeter inside diameter, 1 micrometer film thickness
Method:
split injection: 17/1 split ratio
Autosampler: 1.13 microliters per injection
Column flow: 1.10 milliLiters per minute
Air Flow: 345 milliLiters per minute
Inlet Temperature: 245 degrees Centigrade
Detector Temperature: 285 degrees Centigrade
Initial Temperature=50 degrees Centigrade, 5 degrees Centigrade per minute ramp rate, final temperature=280 degrees Centigrade, Final time=6 minutes
Leading assumptions: 12 seconds per sniff, GC air adds to sample dilution

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Example 1

Synthesis of Table 1 Molecules

Synthesis of Table 1 Molecule No. 1

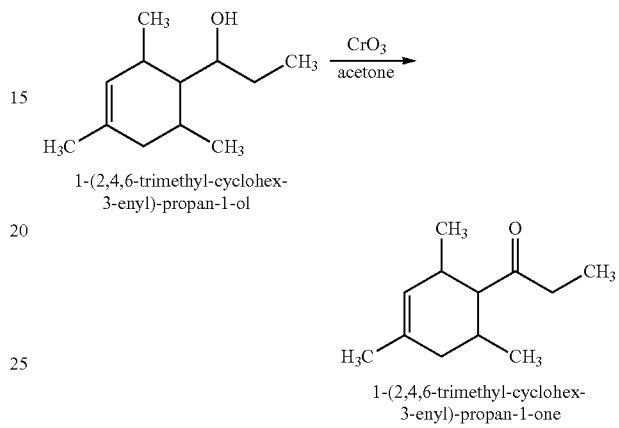

Preparation of 1-(2,4,6-trimethyl-cyclohex-3-enyl)-propan-1-one 1-(2,4,6-Trimethyl-cyclohex-3-enyl)-propan-1-ol (182 g, 1.0 mol) dissolved in acetone (400 mL) was added dropwise to a solution of chromium trioxide ($CrO_3$, 108 g, 1.08 mol) in aqueous sulfuric acid ($H_2SO_4$, 400 mL, 172 g in water) at −10° C. The resulting mixture was aged for 2 hours as the mixture warmed to 0° C. The mixture was then diluted with water and extracted with toluene. The organic layer was concentrated by rotary evaporation and distilled via fractionation to provide 1-(2,4,6-trimethyl-cyclohex-3-enyl)-propan-1-one (113 g, 63% yield) as a colorless liquid.

$^1$H NMR and $^{13}$C NMR data matched those reported previously (See, *J. Am. Chem. Soc.* 1997, 119, pages 3507-3512).

Synthesis of Table 1 Molecule No. 2

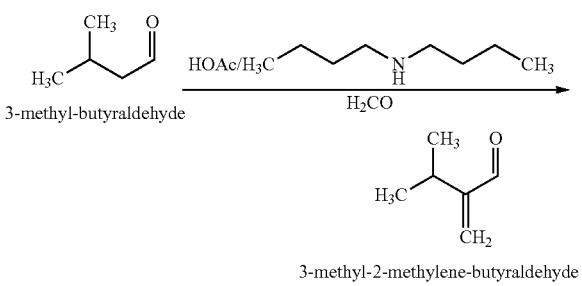

Preparation of 3-methyl-2-methylene-butyraldehyde

Di-n-butylamine (75 g, 0.58 mol) and acetic acid (70 g, 1.16 mol) were mixed in a 5 L round bottom flask. Formaldehyde (1.411 Kg, 17.4 mol) was then added and the resulting mixture was heated to 50° C. Isovaleraldehyde (1 Kg, 11.6 mol) was fed into the reaction mixture at 50° C. for over 2.5 hours. After the feed was completed, gas chromatograph analysis (GC analysis) indicated that the reaction was 92% complete. The reaction mixture containing 3-methyl-2-methylene-butyraldehyde was cooled to room temperature and washed with a saturated sodium carbonate solution.

was added. 1-Isopropyl-2,4-dimethyl-cyclohex-3-enecarbaldehyde (obtained as detailed above) was then fed for over 2 hours at 0° C. under nitrogen. The reaction mixture was aged at 0° C. for another 3 hours and then quenched by pouring the reaction mixture onto a sulfuric acid solution (10%) on crushed ice. The organic layer was separated, washed with sodium carbonate solution, and distilled to provide (1-isopropyl-2,4-dimethyl-cyclohex-3-enyl)-methanol.

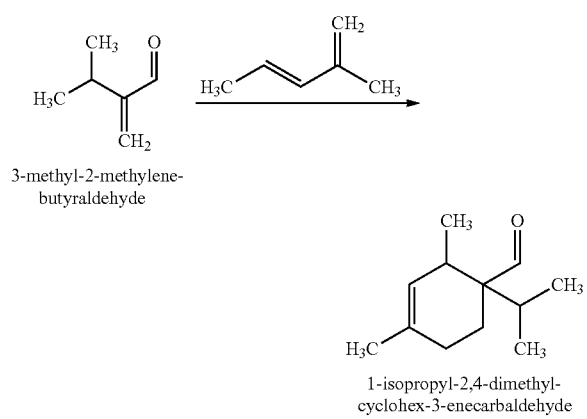

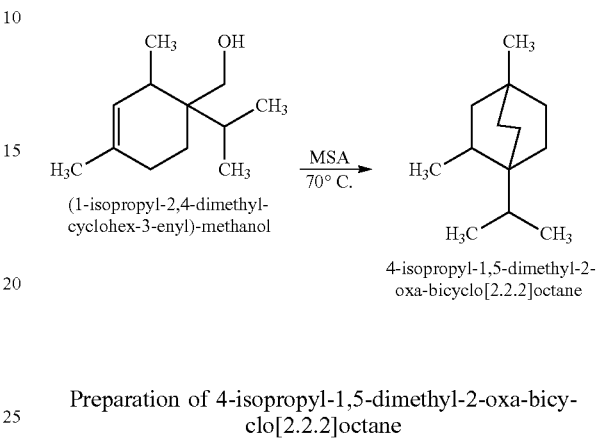

Preparation of 4-isopropyl-1,5-dimethyl-2-oxa-bicyclo[2.2.2]octane

Preparation of 1-isopropyl-2,4-dimethyl-cyclohex-3-enecarbaldehyde

Methylpentadiene (428 g, 5.1 mol) was placed in a stainless-steel autoclave containing the reaction mixture of 3-methyl-2-methylene-butyraldehyde (500 g, 5.1 mol, obtained as detailed above) and heated to 200° C. The reaction was monitored by GC analysis and stopped when a 75% conversion rate was observed. The resulting mixture was then cooled to room temperature and removed from the autoclave. The crude product 1-isopropyl-2,4-dimethyl-cyclohex-3-enecarbaldehyde was dissolved in toluene and azeotroped to dryness under a reduced pressure.

(1-Isopropyl-2,4-dimethyl-cyclohex-3-enyl)-methanol (165 g, 0.9 mol, obtained as detailed above) was dissolved in toluene with methanesulfonic acid (MSA, 5 g, 0.05 mol). The resulting solution was heated to 70° C. and aged at 70° C. for 2 hours. GC analysis showed the completion of cyclization. The reaction mixture was cooled to room temperature, washed with sodium carbonate solution, and distilled to provide 4-isopropyl-1,5-dimethyl-2-oxa-bicyclo [2.2.2]octane.

Synthesis of Table 1 Molecule No. 3

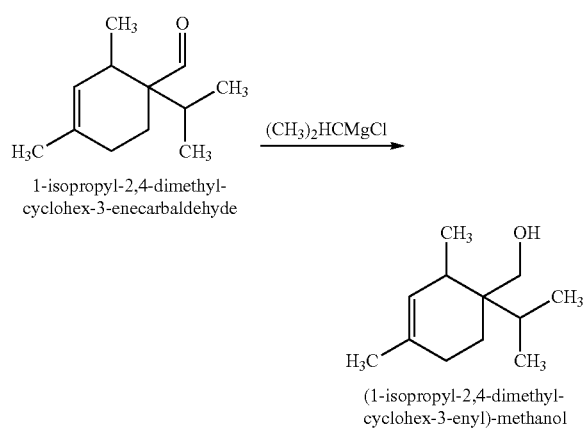

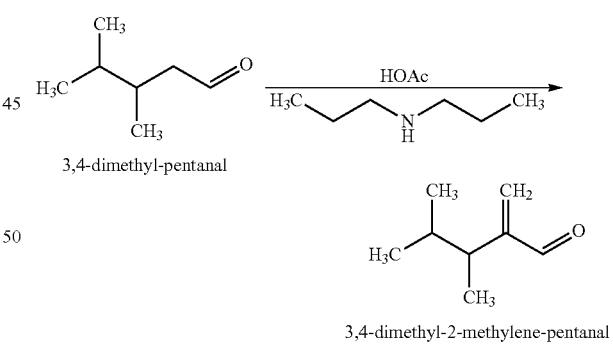

Preparation of 3,4-dimethyl-2-methylene-pentanal

Preparation of (1-isopropyl-2,4-dimethyl-cyclohex-3-enyl)-methanol

Isopropylmagnesium chloride ((CH$_3$)$_2$HCMgCl) in tetrahydrofuran (THF) (1.6 L, 3.2 mol) was loaded into a flame-dried 5 L round bottom flask. Additional THF (1 L)

Dibutylamine (34 g), acetic acid (15.78 g), and formaldehyde (230 g) were charged to a reaction flask and heated to 70° C. 3,4-Dimethyl-pentanal (500 g) was fed over 2 hours and aged for another hour. The reaction mixture was cooled down and toluene (200 mL) was added. The reaction mixture was sequentially washed with water (2 L), sodium carbonate solution (1 L), and brine (1 L) to provide the crude product 3,4-dimethyl-2-methylene-pentanal.

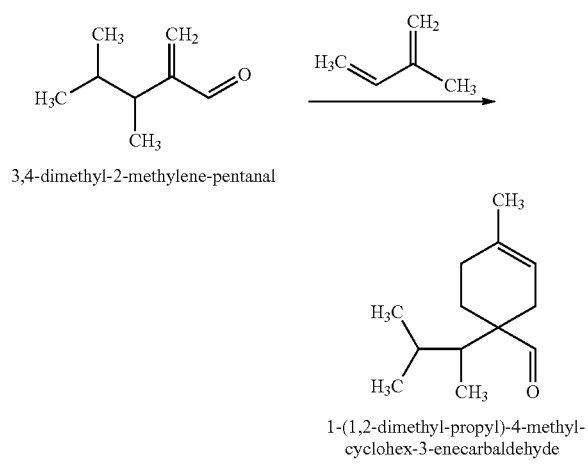

3,4-dimethyl-2-methylene-pentanal 1-(1,2-dimethyl-propyl)-4-methyl-cyclohex-3-enecarbaldehyde

Preparation of 1-(1,2-dimethyl-propyl)-3-methyl-cyclohex-3-enecarbaldehyde 3,4-Dimethyl-2-methylene-pentanal (550 g, obtained as detailed above) and 393 g of isoprene were charged to a Parr Bomb, heated to 160° C., and aged for 12 hours. The rushed over material provided ~32% recovery of 1-(1,2-dimethyl-propyl)-4-methyl-cyclohex-3-enecarbaldehyde (415 g).

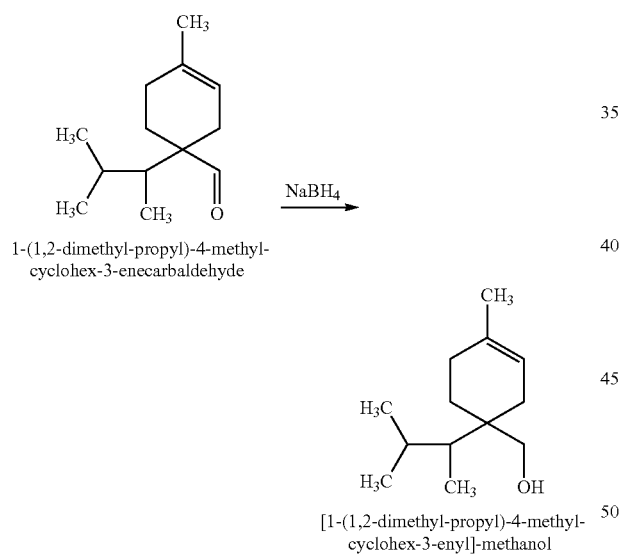

1-(1,2-dimethyl-propyl)-4-methyl-cyclohex-3-enecarbaldehyde

[1-(1,2-dimethyl-propyl)-4-methyl-cyclohex-3-enyl]-methanol

Preparation of [1-(1,2-dimethyl-propyl)-4-methyl-cyclohex-3-enyl]-methanol 1-(1,2-Dimethyl-propyl)-4-methyl-cyclohex-3-enecarbaldehyde (415 g) and methanol (300 mL) were charged into a reaction flask. Sodium borohydride (15 g) was added slowly and the temperature was kept at 35° C. with an ice bath. The reaction mixture was aged for 2 hours and quenched onto HCl (42 g) and ice and extracted with toluene. The reaction mixture was washed until neutral. The rushed over material provided the recovery of [1-(1,2-dimethyl-propyl)-4-methyl-cyclohex-3-enyl]methanol (366 g).

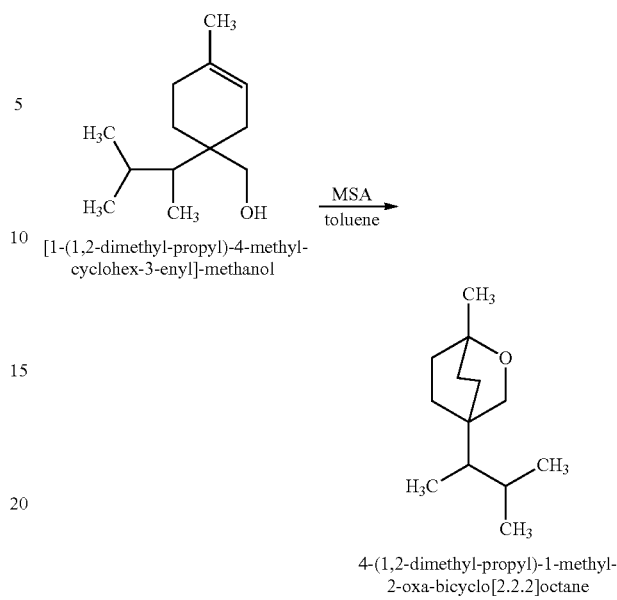

[1-(1,2-dimethyl-propyl)-4-methyl-cyclohex-3-enyl]-methanol 4-(1,2-dimethyl-propyl)-1-methyl-2-oxa-bicyclo[2.2.2]octane

Preparation of 4-(1,2-dimethyl-propyl)-1-methyl-2-oxa-bicyclo[2.2.2]octane

[1-(1,2-Dimethyl-propyl)-4-methyl-cyclohex-3-enyl]-methanol (268 g, obtained as detailed above), MSA (10 g), and toluene (300 mL) were charged to a 2 L reaction flask, heated to 60° C., and aged for 12 hours. The reaction mixture was cooled, washed with saturated sodium carbonate solution, and distilled to provide 4-(1,2-dimethyl-propyl)-1-methyl-2-oxa-bicyclo[2.2.2]octane (146 g).

Synthesis of Table 1 Molecule No. 4

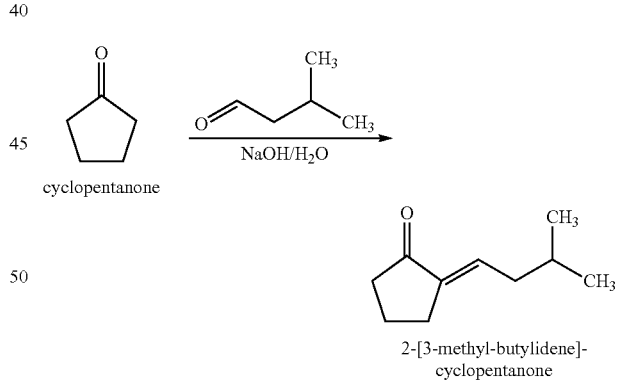

cyclopentanone

2-[3-methyl-butylidene]-cyclopentanone

Preparation of 2-[3-methyl-butylidene]-cyclopentanone

Water (1.9 L) and sodium hydroxide (NaOH, 40 g, 50% caustic) were charged in a flask and heated to 80° C. A premix of cyclopentanone (840 g, 10 mol) and isovaleraldehyde (1.05 Kg, 12 mol) was slowly fed for over 5 hours. The reaction mixture was aged at 80° C. for another 30 minutes, cooled to room temperature, and quenched with acetic acid (120 g, 2 mol). A rushover process provided the crude product 2-[3-methyl-butylidene]-cyclopentanone.

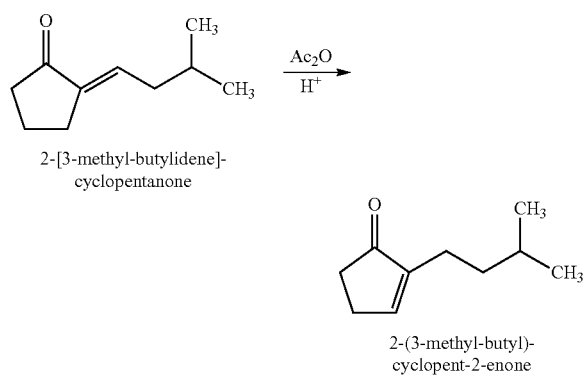

2-[3-methyl-butylidene]-cyclopentanone 2-(3-methyl-butyl)-cyclopent-2-enone

Preparation of 2-(3-methyl-butyl)-cyclopent-2-enone 2-(3-Methyl-butyllidene)-cyclopentanone (1.093 Kg, 7.19 mol, obtained as detailed above), acetic anhydride (300 mL, 3.17 mol), p-toluenesulfonic acid (PTSA, 10 g), and toluene (500 mL) were charged into a flask and heated to 120-130° C. When gas chromatography analysis indicated the completion of the reaction, the reaction mixture was cooled to room temperature and quenched with $Na_2CO_3$ solution (100 mL). The resulting mixture was washed twice with brine (1 L). A rushover process provided the crude product 2-(3-methyl-butyl)-cyclopent-2-enone.

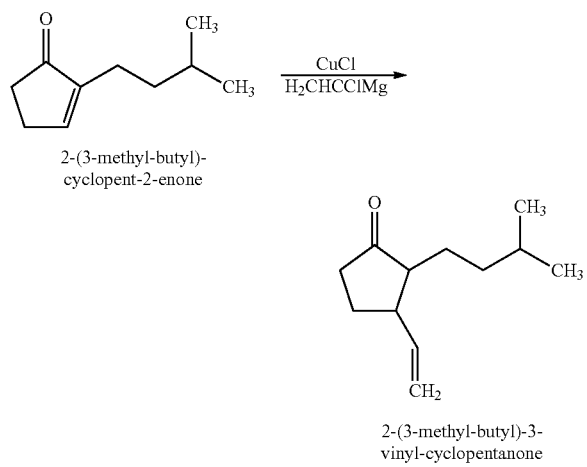

2-(3-methyl-butyl)-cyclopent-2-enone 2-(3-methyl-butyl)-3-vinyl-cyclopentanone

Preparation of 2-(3-methyl-butyl)-3-vinyl-cyclopentanone

Vinylmagnesium chloride ($H_2CHCClMg$, 1 L) and cuprous chloride were charged to a dried flask under nitrogen and cooled to −25° C. with a dry ice bath. The resulting mixture was fed with 2-(3-methyl-butyl)-cyclopent-2-enone (226 g, 1.49 mol, obtained as detailed above) slowly for over 4 hours, aged for another 4 hours, and allowed to warm to 0° C. The reaction mixture was then poured into acetic acid solution and washed to neutral with saturated $Na_2CO_3$ solution. The distillation process provided the product 2-(3-methyl-butyl)-3-vinyl-cyclopentanone.

Synthesis of carboxylic acids used for the synthesis of Table 1 Molecule No. 5

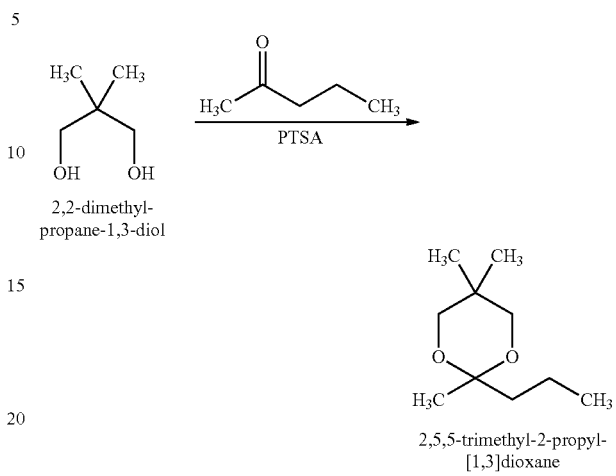

2,2-dimethyl-propane-1,3-diol 2,5,5-trimethyl-2-propyl-[1,3]dioxane

Preparation of 2,5,5-trimethyl-2-propyl-[1,3]dioxane

2-Pentanone, 2,2-dimethyl-propane-1,3-diol, and a catalytic amount of p-toluenesulfonic acid (PTSA) were refluxed in toluene to provide a crude product. Distillation provided the product 2,5,5-trimethyl-2-propyl-[1,3]dioxane.

$^1$HNMR: 3.54 ppm (d, 2H, J=11.1 Hz), 3.44 ppm (d, 2H, J=10.7 Hz), 1.67 ppm (m, 2H), 1.44 ppm (m, 2H), 1.35 ppm (s, 3H), 1.00 ppm (s, 3H), 0.93 ppm (t, 3H, J=7.4 Hz), 0.90 ppm (s, 3H)

Synthesis of Table 1 Molecule No. 6

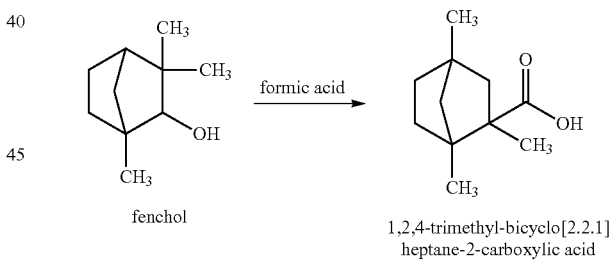

fenchol 1,2,4-trimethyl-bicyclo[2.2.1]heptane-2-carboxylic acid

Preparation of 1,2,4-trimethyl-bicyclo[2.2.1]heptane-2-carboxylic acid

A solution of fenchol (179 g) in formic acid (90%, 157 g) was added to sulfuric acid (98%) at 0-15° C. with slow stirring. Upon finish, the reaction mixture was stirred for another 2 hours and then poured into ice. The reaction mixture was extracted three times with toluene (100 mL). The organic phases were combined and extracted with aqueous sodium hydroxide (10%, 500 mL). The organic phase was discarded. The aqueous phase was acidified with sulfuric acid till pH<1, and then extracted with toluene. The resulting organic phase was concentrated to provide 1,2,4-trimethyl-bicyclo[2.2.1]heptane-2-carboxylic acid (135 g, 73% yield) as a white solid.

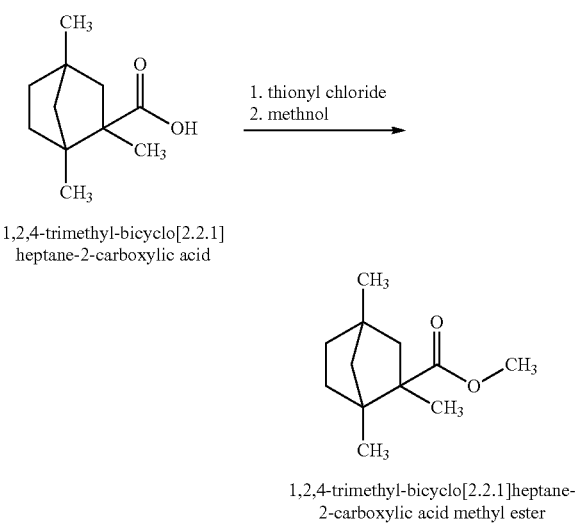

1,2,4-trimethyl-bicyclo[2.2.1]
heptane-2-carboxylic acid 1,2,4-trimethyl-bicyclo[2.2.1]heptane-
2-carboxylic acid methyl ester Preparation of
1,2,4-trimethyl-bicyclo[2.2.1]heptane-2-carboxylic
acid methyl ester 1,2,4-Trimethyl-bicyclo[2.2.1]heptane-2-carboxylic acid (obtained as detailed above) was dissolved in methylene chloride (50 mL), and added dropwise to thionyl chloride (100 mL) at 50° C. After 1 hour, excessive thionyl chloride was distilled out and methanol (100 mL) was added. The reaction mixture was stirred overnight and then poured into saturated aqueous sodium bicarbonate. The resulting mixture was extracted with toluene and the organic phase was distilled to provide 1,2,4-trimethyl-bicyclo[2.2.1]heptane-2-carboxylic acid methyl ester (65 g, 45% yield).

Synthesis of Table 1 Molecule No. 7

Preparation of
8-hydroxy-2,6-dimethyl-nona-2,6-diene

Methyl lithium in tetrahydrofuran (THF) (1.6 L, 1 M) was charged to a flame dried 3 L reaction flask equipped with a thermometer, a mechanical stirrer, condenser, and an addition funnel. Citral was added dropwise for over 2-2.5 hours. The reaction mixture was aged until the conversion rate was greater than 90%. The reaction mixture was cooled to lower than 30° C. and quenched by the slow addition of HCl (pH<5.10%). The aqueous phase was extracted three times with toluene (100 mL) and the extracts were added to the crude reaction mixture. The crude reaction mixture was then washed with saturated sodium bicarbonate (500 mL) followed by saturated salt solution and dried over anhydrous sodium sulphate. The crude reaction mixture was concentrated. The solvents were recovered via a rotary evaporator to provide 8-hydroxy-2,6-dimethyl-nona-2,6-diene.

Preparation of
8-ethoxy-2,6-dimethyl-nona-2,6-diene

THF (500 mL) and sodium hydride (60%, 52 g, 1.3 mol) were charged to a flame dried 2 L reaction flask equipped with a thermometer, a mechanical stirrer, a condenser, and an addition funnel. 8-Hydroxy-2,6-dimethyl-nona-2,6-diene (obtained as detailed above) was added dropwise while allowing the temperature to rise no higher than 50° C. After the addition was completed, the reaction mixture was aged for 1 hour. Ethyl bromide (142 g, 1.3 mol.) was added dropwise for over 2 hours. The reaction mixture was then heated to 60° C. and aged until the conversion rate was shown to be over 90%. The reaction mixture was cooled to lower than 30° C. and quenched by the slow addition of HCl (pH<5, 10%). The layers were split. The aqueous phase was extracted three times with toluene (100 mL). The extracts were added to the crude reaction mixture, which was then washed with saturated sodium bicarbonate followed by saturated salt solution and dried over anhydrous sodium sulphate. The crude reaction mixture was concentrated. The solvents were recovered via a rotary evaporator. Fractional distillation provided the compound 8-ethoxy-2,6-dimethyl-nona-2,6-dien with a boiling point of 125° C. at a pressure of 4.5 mmHg.

$^1$HNMR: 5.06-5.13 ppm (m, 2H); 4.09-4.18 ppm (m, 1H); 3.43-3.53 ppm (m, 1H); 3.27-3.37 ppm (m, 1H); 2.00-2.16 ppm (m, 4H); 1.60-1.74 ppm (m, 9H); 1.15-1.20 ppm (m, 6H).

Synthesis of Table 1 Molecule No. 8

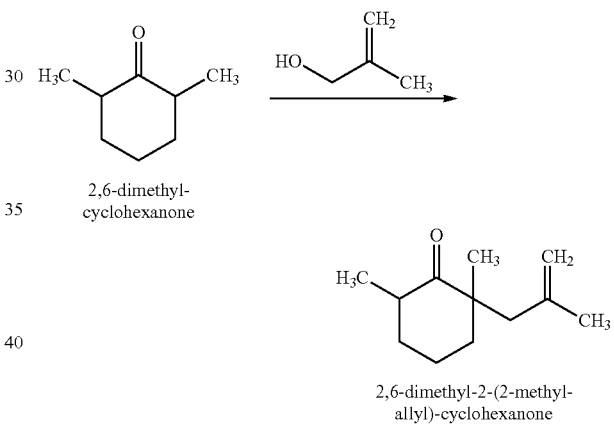

2,6-dimethyl-
cyclohexanone 2,6-dimethyl-2-(2-methyl-
allyl)-cyclohexanone

Preparation of
2,6-dimethyl-2-(2-methyl-allyl)-cyclohexanone 2,6-Dimethyl-cyclohexanone (1 kg, 4 mol), trimethyl orthoformate (TMOF, 880 g), and methanol (800 mL) were charged to a 5 L reaction flask. HCl was added quickly. Reaction exothermed and the temperature increased from 14° C. to 20° C. The reaction mixture was heated to 60° C. and aged for 7 hours. When the reaction was about 75% complete, the reaction mixture was quenched with $NaOCH_3$ (25%, 25 g), heated to 90° C., and applied to a Bidwell-Sterling trap. The reaction mixture was then cooled to room temperature followed by sequential addition of methallyl alcohol (1.25 Kg, 8.5 moles), HOAc (50 g), and methane sulfonic acid (MSA, 10 g). The resulting mixture was heated to 110° C., applied to a Bidwell-Sterling trap, and aged for 4 hours until gas chromatograph analysis indicated that the reaction was 95% completed. The reaction mixture was then cooled and washed with saturated sodium carbonate solution (3 L) to provide the crude product 2,6-dimethyl-2-(2-methyl-allyl)-cyclohexanone.

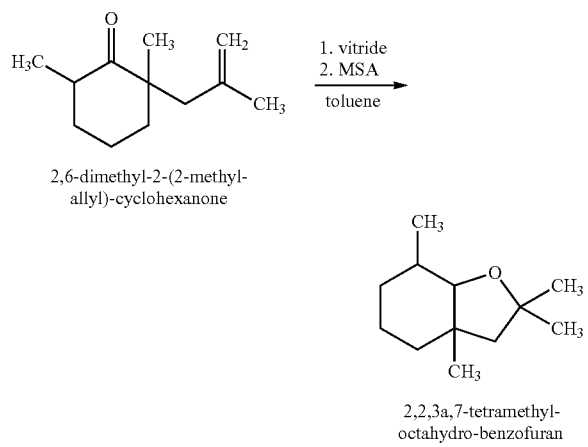

2,6-dimethyl-2-(2-methyl-allyl)-cyclohexanone 2,2,3a,7-tetramethyl-octahydro-benzofuran

Preparation of 2,2,3a,7-tetramethyl-octahydro-benzofuran

A 3 L reaction flask was charged with vitride (325 g, 0.9 mol) and toluene (500 mL), heated to 100° C., fed with 2,6-dimethyl-2-(2-methyl-allyl)-cyclohexanone (200 g, 1.1 mol, obtained as detailed above) for over 2 hours, and aged for another 2 hours. After the reaction completed, the reaction mixture was cooled to room temperature, quenched with IPA (100 mL). NaOH (50%, 300 g) and water (200 mL) were then added, heated to 80° C., and aged for another hour. The reaction mixture was cooled to room temperature and more water (200 mL) was added. Layers were split to dispose the aqueous waste. The organic layer was charged back to the flask. Toluene (300 mL) was added and water was removed with a Bidwell-Sterling trap through azeotrope. The resulting mixture was cooled to 50° C. MSA (28 g, 0.3 mol) was added and the reaction mixture was heated to reflux. The consumption of the starting material was indicated after 3 hours. The resulting mixture was then cooled to room temperature and washed with saturated sodium carbonate solution (1 L) followed by brine (1 L). Distillation and fractionation provided the product 2,2,3a,7-tetramethyl-octahydro-benzofuran (125 g).

Synthesis of Table 1 Molecule No. 9

Preparation of 3a-isopropyl-2,6-dimethyl-octahydro-benzofuran

Menthone (500 g), trimethylorthoformate (377 g) and methanol (400 mL) were charged to a 3 L reaction flask. In one portion, hydrochloric acid (3 g) was added and the mixture exothermed from 22° C. to 40° C. The reaction mixture was aged 6 hours and quenched with sodium methoxide solution (35 g). Low boiling materials were removed while the reaction mixture was heated to 90° C. Allyl alcohol (404 g) and acetic acid (195 g) were added and the reaction mixture was heated to 160° C. The reaction mixture was held at 160° C. for 3 hours, cooled to 25° C., and washed with brine (500 mL). The crude product was distilled to provide a mixture of allyl menthone isomers.

Red-Al® (397 g) was charged to a 2 L reaction flask and heated to 55° C. Allyl menthone isomers (248 g, obtained in above) were fed into the flask and the reaction was allowed to exotherm to 70° C. The reaction mixture was aged for 8 hours and quenched with isopropanol (100 mL) followed by aqueous sodium hydroxide solution (50%, 307 g). The resulting organic layer was washed with brine (500 mL). The crude alcohol was distilled to provide a mixture of allyl menthol isomers.

Allyl menthol isomers (200 g, obtained in above), toluene (500 mL), and methanesulfonic acid (MSA, 5 g) were charged to 1 L reaction flask. The reaction mixture was heated to 80° C., aged for 8 hours, then cooled to 22° C., and washed with aqueous sodium carbonate solution (10%, 300 mL). The resulting crude mixture was purified by distillation to afford 3a-isopropyl-2,6-dimethyl-octahydro-benzofuran.

Synthesis of Table 1 Molecule No. 10

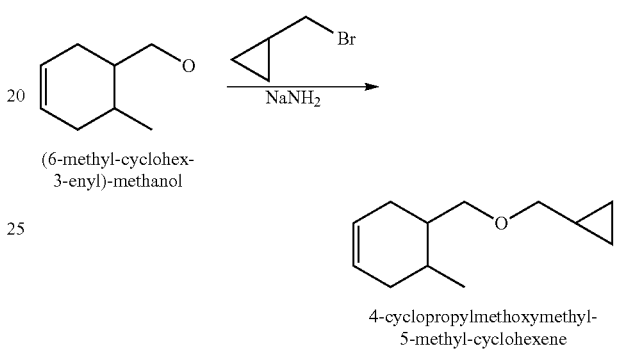

(6-methyl-cyclohex-3-enyl)-methanol 4-cyclopropylmethoxymethyl-5-methyl-cyclohexene

Preparation of 4-cyclopropylmethoxymethyl-5-methyl-cyclohexene

A reaction flask was charged with tetrahydrofuran (THF, 500 mL) and sodium amide ($NaNH_2$, 100 g, 2.6 mol) and heated to reflux (~65° C.). (6-Methyl-cyclohex-3-enyl)-methanol (300 g, 2.3 mol) was fed in. The reaction mixture was aged for a half-hour. Bromomethyl-cyclopropane (526 g, 3.9 mol) was then fed for over 2 hours at the reflux temperature. The reaction was monitored by gas chromatography. A sample the reaction mixture was quenched in isopropyl alcohol, water, and toluene. After the feed of bromomethyl-cyclopropane was completed, the reaction was aged for a total of 6 hours. The reaction mixture was then cooled to 10° C. and quenched with isopropyl alcohol (100 mL), water (1 L), and toluene (500 mL). On the work-up, the reaction mixture was acidified with HCl (300 mL) and washed with sodium carbonate solution (5%, 500 mL) in a separatory funnel followed with warm $H_2O$ until the pH was neutral. Distillation of the resulting mixture provided the product 4-cyclopropylmethoxymethyl-5-methyl-cyclohexene.

Synthesis of Table 1 Molecule No. 11

Preparation of cyclopropanecarboxylic acid 1-methyl-hexyl ester

2-Heptanol (200 g, 1.72 mol) and cyclopropanecarboxylic acid (163 g, 1.90 mol) were added into toluene (500 mL), followed by p-toluenesulfonic acid (3.2 g, 0.0172 mol). The reaction mixture was heated to reflux for 6 hours, cooled to room temperature, and quenched with aqueous sodium bicarbonate (1 L). The reaction mixture was then washed with brine (0.5 L) and dried over sodium sulfate (50 g). The solvent was removed and the reaction mixture was distilled to provide the product cyclopropanecarboxylic acid 1-methyl-hexyl ester (253 g).

Synthesis of Table 1 Molecule No. 12

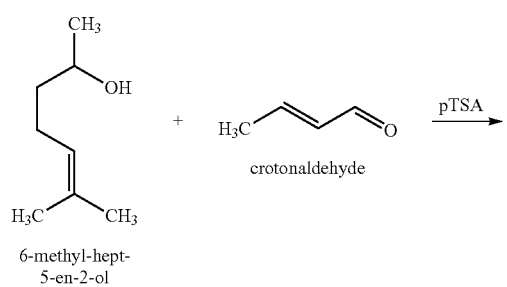

6-methyl-hept-5-en-2-ol crotonaldehyde 3-isopropenyl-6-methyl-2 propenyl-tetrahydro-pyran Preparation of 3-isopropyl-6-methyl-2-propenyl-tetrahydro-pyran 6-Methyl-hept-5-en-2-ol (512 g, 3.8 mol, 96%), toluene (750 ml), and p-toluenesulfonic acid (pTSA, 2.6 g) were charged in a flask and heated to 122° C. Crotonaldehyde (350 g, 5 mol) was fed into the mixture for over 3-4 hours at reflux. Water was removed with a Bidwell-Sterling trap. The reaction mixture was aged for 1 hour. Standard addition and gas chromatography (GC) analysis indicated that about 11% of the starting material 6-methyl-hept-5-en-2-ol was left. Additional crotonaldehyde (35 g, 0.5 mol) was added. The reaction mixture was at reflux for another 45 minutes. About 70 ml water was collected and the final temperature was about 118° C. GC analysis indicated that about 8% of the starting material 6-methyl-hept-5-en-2-ol was left. The reaction mixture was quenched with water and wash one time with dilute carbonate solution. The consequent rush-over process provided the product 3-isopropyl-6-methyl-2-propenyl-tetrahydro-pyran (493 g) with a boiling point of 109 C at a pressure of 25 mmHg.

Synthesis of Table 1 Molecule No. 13

Preparation of acetic acid 3-isopropyl-1,2-dimethyl-cyclopentyl ester

Trans-dihydroplinol (165 g) and dimethylaminopyridine (2 g) were charged into a 1 L round bottom flask and heated to 80° C. Acetic anhydride (143 g) was added to the resulting mixture and was stirred at the same temperature until the majority of the starting material was consumed. The reaction mixture was then cooled to room temperature, washed with water and sodium carbonate, and extracted with toluene. The organic solvents were removed in vacuo and fractional distillation provided the product acetic acid 3-isopropyl-1, 2-dimethyl-cyclopentyl ester (45 g, 21% yield).

Synthesis of Table 1 Molecule No. 14

Preparation of 4-(2,4-dimethyl-cyclohex-3-enylidene)-butan-2-one

Ketoester (780 g) was added into a 2 L round bottom flask and heated to 200° C. Water (2 equivalents) was added drop-wise and the lighter solvent was removed via a Bidwell-Sterling trap. The reaction mixture was then cooled to room temperature. The crude product was dried over anhydrous sodium sulfate. Fractional distillation provided product 4-(2,4-dimethyl-cyclohex-3-enylidene)-butan-2-one (231 g).

Synthesis of Table 1 Molecule No. 15

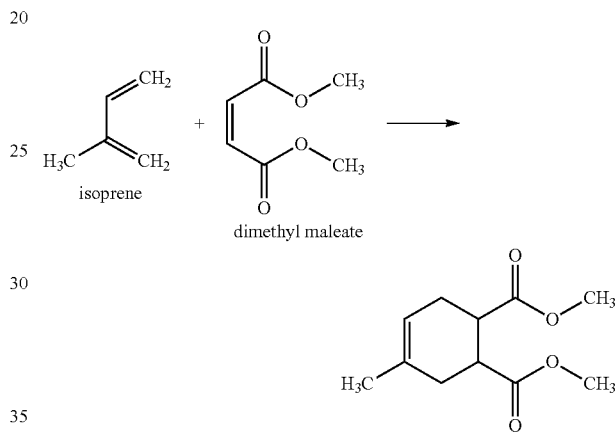

isoprene dimethyl maleate 4-methyl-cyclohex-4-ene-1,2-dicarboxylic acid dimethyl ester Preparation of 4-methyl-cyclohex-4-ene-1,2-dicarboxylic acid dimethyl ester Isoprene (350 g, 5.1 mol) and dimethyl maleate (741 g, 5.1 mol) were loaded into a stainless steel autoclave. The autoclave was sealed and heated to 150° C. The temperature of the autoclave increased to 195° C. due to the heat of the reaction. The temperature was held at 160° C. for 1 hour. Gas chromatography (GC) analysis indicated the completion of the reaction. The autoclave was then cooled to room temperature. Simple distillation of the resulting mixture provided 4-methyl-cyclohex-4-ene-1,2-dicarboxylic acid dimethyl ester (725 g, 3.4 mol, 66% yield) as a light yellow liquid.

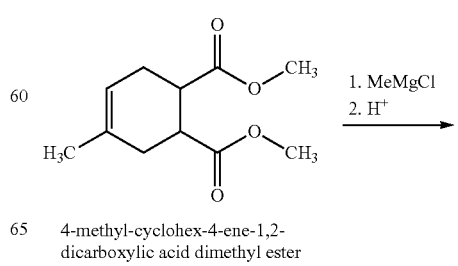

4-methyl-cyclohex-4-ene-1,2-dicarboxylic acid dimethyl ester

1. MeMgCl
2. H⁺

-continued

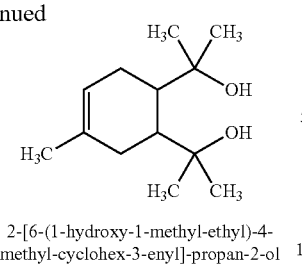

2-[6-(1-hydroxy-1-methyl-ethyl)-4-methyl-cyclohex-3-enyl]-propan-2-ol

Preparation of 2-[6-(1-hydroxy-1-methyl-ethyl)-4-methyl-cyclohex-3-enyl]-propan-2-ol Methylmagnesium chloride (MeMgCl, 3 M, 4.6 L, 13.6 mol) and tetrahydrofuran (THF, 2.5 L) were placed in a 12 L round bottom flask under nitrogen. The resulting solution was cooled to 0-10° C. using an automatic dry ice bath. The 4-methyl-cyclohex-4-ene-1,2-dicarboxylic acid dimethyl ester (725 g, 3.4 mol, obtained as detailed above) was then fed into the reaction flask under nitrogen while the temperature was held steady. The completion of the reaction was monitored by GC analysis. After the feed was complete, the reaction mixture was quenched by pouring onto sulfuric acid solution (10%) and ice. The resulting layers were then split and the organic layers were washed with saturated sodium carbonate solution. The resulting mixture was then reduced in volume using a rotovap to provide the crude product 2-[6-(1-hydroxy-1-methyl-ethyl)-4-methyl-cyclohex-3-enyl]-propan-2-ol (720 g, 3.3 mol).

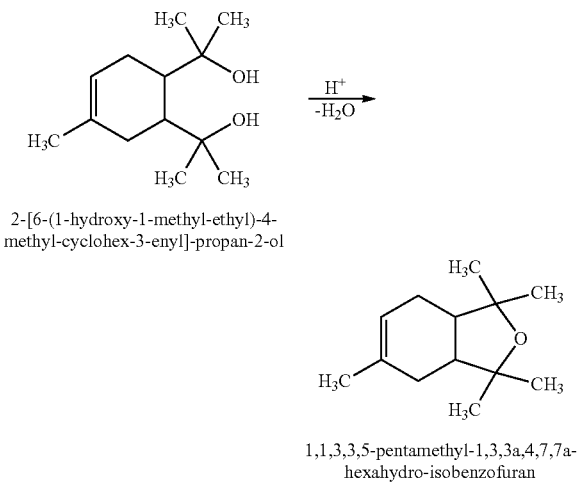

2-[6-(1-hydroxy-1-methyl-ethyl)-4-methyl-cyclohex-3-enyl]-propan-2-ol 1,1,3,3,5-pentamethyl-1,3,3a,4,7,7a-hexahydro-isobenzofuran Preparation of 1,1,3,3,5-pentamethyl-1,3,3a,4,7,7a-hexahydro-isobenzofuran 2-[6-(1-Hydroxy-1-methyl-ethyl)-4-methyl-cyclohex-3-enyl]-propan-2-ol (720 g, 3.3 mol, obtained as detailed above) was loaded into a round bottom flask fitted with a Bidwell-Sterling trap and dissolved in toluene (1 L). An acid catalyst p-toluenesulfonic acid (pTSA, 40 g, 0.18 mol) was added and the mixture was heated to reflux. The reflux was maintained for 1.5 hours. Water was collected in the Bidwell-Sterling trap during this period. GC analysis indicated the completion of the reaction. The resulting mixture was reduced in volume and purified by fractional distillation to provide 1,1,3,3,5-pentamethyl-1,3,3a,4,7,7a-hexahydro-isobenzofuran (60 g, 9% yield).

Synthesis of Table 1 Molecule No. 16

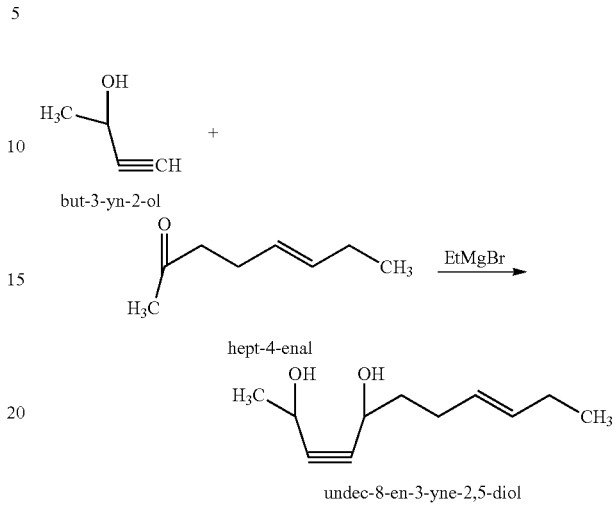

Preparation of undec-8-ene-2,5-diol

But-3-yn-2-ol was added into a solution of ethyl magnesium bromide (EtMgBr) in tetrahydrofuran (THF). Hept-4-enal was then dropped into the mixture at room temperature and aged for 2 hours. The rush over process provided the product undec-8-en-3-yne-2,5-diol.

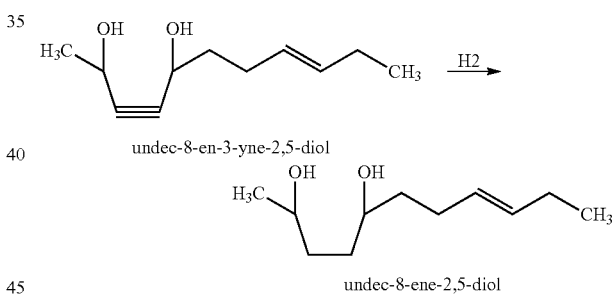

Preparation of undec-8-ene-2,5-diol

Undec-8-en-3-yne-2,5-diol (obtained as detailed above) was hydrogenated under hydrogen and 10 percent palladium on barium sulphate and quinoline. The rush over process provided the product undec-8-ene-2,5-diol.

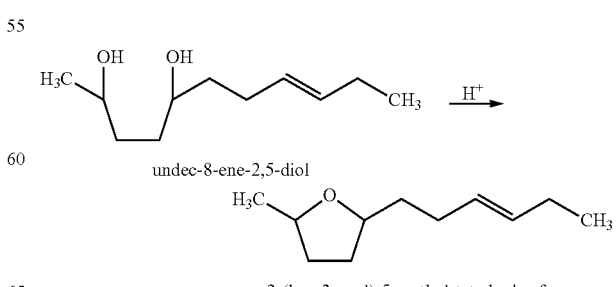

Preparation of 2-(hex-3-enyl)-5-methyl-tetrahydro-furan

Undec-8-ene-2,5-diol (obtained as detailed above) was heated to 150° C. with KHSO4. The resulting mixture was distilled to provide the product 2-(hex-3-enyl)-5-methyl-tetrahydro-furan.

Synthesis of Table 1 Molecule No. 17

3-sec-Butyl-1,5-dimethyl-2-oxa-bicyclo[2.2.2]octane may be prepared by the process disclosed in U.S. Pat. No. 4,197,328 to Schmitt et al.

Synthesis of Table 1 Molecule No. 18

1-(6-Isopropyl-2-methyl-cyclohex-3-enyl)-ethanone may be prepared by the process disclosed in European Patent Application No. 0231556 (A1) to Van der Weerdt et al.

Synthesis of Table 1 Molecule No. 19

1-(6-Isopropyl-4-methyl-cyclohex-3-enyl)-ethanone may be prepared by the process disclosed in U.S. Pat. No. 4,524,020 to Spreker at al.

Synthesis of Table 1 Molecule No. 20

4-(3-Methoxy-1-methyl-propyl)-1-methyl-cyclohexene may be prepared by the process disclosed in European Patent Application No. 53716 A1 to Schaper et al.

Synthesis of Table 1 Molecule No. 21

3-(1,1-Dimethoxy-ethyl)-1,1-dimethyl-cyclohexane may be prepared by the process disclosed in U.S. Pat. No. 4,933,320 to Spreker et al.

Synthesis of Table 1 Molecule No. 22

2,4-Dimethyl-2-(4-methyl-pent-3-nyl)-[1,3]dioxolane may be prepared by the process disclosed in *Huaxue Yanjiu Yu Yingyong*, 2003, pp 229-230, to Peng, A., Xia, M., Jin, X.

Example 2

Preformed Amine Reaction Product

The following ingredients are weighted off in a glass vial:
1. 50% of the perfume material comprising one or more Table 1 PRMs
2. 50% of Lupasol WF (CAS#09002-98-6) from BASF, is put at 60° C. in warm water bath for 1 hour before use.

Mixing of the two ingredients is done by using the Ultra-Turrax T25 Basic equipment (from IKA) during 5 minutes. When the mixing is finished the sample is put in a warm water bath at 60° C. for ±12 hours. A homogenous, viscous material is obtained.

In the same way as described above different ratios between the components can be used:

| | Weight % | | | | |
|---|---|---|---|---|---|
| Perfume Material | 40 | 50 | 60 | 70 | 80 |
| Lupasol WF | 60 | 50 | 40 | 30 | 20 |

Example 3

84 wt % Core/16 wt % Wall Melamine Formaldehyde (MF) Capsule (PAD Reservoir System 25 grams of butyl acrylate-acrylic acid copolymer emulsifier (Colloid C351, 25% solids, pka 4.5-4.7, (Kemira Chemicals, Inc. Kennesaw, Ga. U.S.A.) is dissolved and mixed in 200 grams deionized water. The pH of the solution is adjusted to pH of 4.0 with sodium hydroxide solution. 8 grams of partially methylated methylol melamine resin (Cymel 385, 80% solids, (Cytec Industries West Paterson, N.J., U.S.A.)) is added to the emulsifier solution. 200 grams of perfume oil comprising one or more Table 1 PRMs is added to the previous mixture under mechanical agitation and the temperature is raised to 50° C. After mixing at higher speed until a stable emulsion is obtained, the second solution and 4 grams of sodium sulfate salt are added to the emulsion. This second solution contains 10 grams of butyl acrylate-acrylic acid copolymer emulsifier (Colloid C351, 25% solids, pka 4.5-4.7, Kemira), 120 grams of distilled water, sodium hydroxide solution to adjust pH to 4.8, 25 grams of partially methylated methylol melamine resin (Cymel 385, 80% solids, Cytec). This mixture is heated to 70° C. and maintained overnight with continuous stirring to complete the encapsulation process. 23 grams of acetoacetamide (Sigma-Aldrich, Saint Louis, Mo., U.S.A.) is added to the suspension. An average capsule size of 30 um is obtained as analyzed by a Model 780 Accusizer.

Example 4

Process of Making a Polymer Assisted Delivery (PAD) Matrix System

A mixture comprising 50% of a perfume composition comprising one or more Table 1 PRMs, 40% of carboxyl-terminated Hycar®1300X18 (CAS#0068891-50-9) from Noveon, (put at 60° C. in warm water bath for 1 hour before mixing) and 10% of Lupasol® WF (CAS#09002-98-6) from BASF (put at 60° C. in warm water bath for 1 hour before mixing). Mixing is achieved by mixing for five minutes using a Ultra-Turrax T25 Basic equipment (from IKA). After mixing, the mixture is put in a warm water bath at 60° C. for ±12 hours. A homogenous, viscous and sticky material is obtained.

In the same way as described above different ratios between the components can be used:

| | Weight % | | | | | | | | | | | |
|---|---|---|---|---|---|---|---|---|---|---|---|---|
| Perfume composition | 40 | 50 | 60 | 70 | 80 | 50 | 50 | 50 | 50 | 50 | 50 | 50 |
| Lupasol ® WF | 12 | 10 | 8 | 6 | 4 | 2.5 | 5 | 7.5 | 10 | 12.5 | 15 | 17.5 | 20 |
| Hycar ® CTBN1300X18 | 48 | 40 | 32 | 24 | 16 | 47.5 | 45 | 42.5 | 40 | 37.5 | 35 | 32.5 | 30 |

Example 5

Product Formulation

Non-limiting examples of product formulations containing PRMs disclosed in the present specification perfume and amines summarized in the following table.

| (% wt) | XI | XII | XIII | XIV | XV | XVI | XVII | XVIII | XIX | XX |
|---|---|---|---|---|---|---|---|---|---|---|
| FSA [a] | 14 | 16.47 | 14 | 12 | 12 | 16.47 | — | — | 5 | 5 |
| FSA [b] | — | — | — | — | — | — | 3.00 | — | — | — |
| FSA [c] | — | — | — | — | — | — | — | 6.5 | — | — |
| Ethanol | 2.18 | 2.57 | 2.18 | 1.95 | 1.95 | 2.57 | — | — | 0.81 | 0.81 |
| Isopropyl Alcohol | — | — | — | — | — | — | 0.33 | 1.22 | — | — |
| Starch [d] | 1.25 | 1.47 | 2.00 | 1.25 | — | 2.30 | 0.5 | 0.70 | 0.71 | 0.42 |
| Amine* | 0.6 | 0.75 | 0.6 | 0.75 | 0.37 | 0.60 | 0.37 | 0.6 | 0.37 | 0.37 |
| Perfume X [e] | 0.40 | 0.13 | 0.065 | 0.25 | 0.03 | 0.030 | 0.030 | 0.065 | 0.03 | 0.03 |
| Phase Stabilizing Polymer [f] | 0.21 | 0.25 | 0.21 | 0.21 | 0.14 | — | — | 0.14 | — | — |
| Suds Suppressor [g] | — | — | — | — | — | — | — | 0.1 | — | — |
| Calcium Chloride | 0.15 | 0.176 | 0.15 | 0.15 | 0.30 | 0.176 | — | 0.1-0.15 | — | — |
| DTPA [h] | 0.017 | 0.017 | 0.017 | 0.017 | 0.007 | 0.007 | 0.20 | — | 0.002 | 0.002 |
| Preservative (ppm) [i,j] | 5 | 5 | 5 | 5 | 5 | 5 | — | 250 [j] | 5 | 5 |
| Antifoam [k] | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Structurant [l] | 0.01 | 0.01 | 0.01 | 0.01 | 0.01 | 0.01 | 0.01 | 0.01 | 0.01 | 0.01 |
| Additional Neat Perfume | 0.8 | 0.7 | 0.9 | 0.5 | 1.2 | 0.5 | 1.1 | 0.6 | 1.0 | 0.9 |
| Deionized Water | † | † | † | † | † | † | † | † | † | † |

[a] N,N-di(tallowoyloxyethyl)-N,N-dimethylammonium chloride.
[b] Methyl bis(tallow amidoethyl)2-hydroxyethyl ammonium methyl sulfate.
[c] Reaction product of Fatty acid with Methyldiethanolamine in a molar ratio 1.5:1, quaternized with Methylchloride, resulting in a 1:1 molar mixture of N,N-bis(stearoyl-oxy-ethyl) N,N-dimethyl ammonium chloride and N-(stearoyl-oxy-ethyl) N,-hydroxyethyl N,N dimethyl ammonium chloride.
[d] Cationic high amylose maize starch available from National Starch under the trade name CATO ®.
[e] Perfume comprising one or more Table 1 PRMs.
[f] Copolymer of ethylene oxide and terephthalate having the formula described in U.S. Pat. No. 5,574,179 at col. 15, lines 1-5, wherein each X is methyl, each n is 40, u is 4, each R1 is essentially 1,4-phenylene moieties, each R2 is essentially ethylene, 1,2-propylene moieties, or mixtures thereof.
[g] SE39 from Wacker
[h] Diethylenetriaminepentaacetic acid.
[i] KATHON ® CG available from Rohm and Haas Co. "PPM" is "parts per million."
[j] Gluteraldehyde
[k] Silicone antifoam agent available from Dow Corning Corp. under the trade name DC2310.
[l] Hydrophobically-modified ethoxylated urethane available from Rohm and Haas under the tradename Aculan 44.
*One or more materials comprising an amine moiety as disclosed in the present specification.
† balance

Example 6

Dry Laundry Formulations

| | % w/w granular laundry detergent composition | | | | | | |
|---|---|---|---|---|---|---|---|
| Component | A | B | C | D | E | F | G |
| Brightener | 0.1 | 0.1 | 0.1 | 0.2 | 0.1 | 0.2 | 0.1 |
| Soap | 0.6 | 0.6 | 0.6 | 0.6 | 0.6 | 0.6 | 0.6 |
| Ethylenediamine disuccinic acid | 0.1 | 0.1 | 0.1 | 0.1 | 0.1 | 0.1 | 0.1 |
| Acrylate/maleate copolymer | 1.5 | 1.5 | 1.5 | 1.5 | 1.5 | 1.5 | 1.5 |
| Hydroxyethane di(methylene phosphonic acid) | 0.4 | 0.4 | 0.4 | 0.4 | 0.4 | 0.4 | 0.4 |

-continued

| Component | % w/w granular laundry detergent composition | | | | | | |
|---|---|---|---|---|---|---|---|
| | A | B | C | D | E | F | G |
| Mono-$C_{12-14}$ alkyl, di-methyl, mono-hydroyethyl quaternary ammonium chloride | 0.5 | 0.5 | 0.5 | 0.5 | 0.5 | 0.5 | 0.5 |
| Linear alkyl benzene | 0.1 | 0.1 | 0.2 | 0.1 | 0.1 | 0.2 | 0.1 |
| Linear alkyl benzene sulphonate | 10.3 | 10.1 | 19.9 | 14.7 | 10.3 | 17 | 10.5 |
| Magnesium sulphate | 0.4 | 0.4 | 0.4 | 0.4 | 0.4 | 0.4 | 0.4 |
| Sodium carbonate | 19.5 | 19.2 | 10.1 | 18.5 | 29.9 | 10.1 | 16.8 |
| Sodium sulphate | 29.6 | 29.8 | 38.8 | 15.1 | 24.4 | 19.7 | 19.1 |
| Sodium Chloride | 0.1 | 0.1 | 0.1 | 0.1 | 0.1 | 0.1 | 0.1 |
| Zeolite | 9.6 | 9.4 | 8.1 | 18 | 10 | 13.2 | 17.3 |
| Photobleach particle | 0.1 | 0.1 | 0.2 | 0.1 | 0.2 | 0.1 | 0.2 |
| Blue and red carbonate speckles | 1.8 | 1.8 | 1.8 | 1.8 | 1.8 | 1.8 | 1.8 |
| Ethoxylated Alcohol AE7 | 1 | 1 | 1 | 1 | 1 | 1 | 1 |
| Tetraacetyl ethylene diamine agglomerate (92 wt % active) | 0.9 | 0.9 | 0.9 | 0.9 | 0.9 | 0.9 | 0.9 |
| Citric acid | 1.4 | 1.4 | 1.4 | 1.4 | 1.4 | 1.4 | 1.4 |
| PDMS/clay agglomerates (9.5% wt % active PDMS) | 10.5 | 10.3 | 5 | 15 | 5.1 | 7.3 | 10.2 |
| Polyethylene oxide | 0.2 | 0.2 | 0.2 | 0.2 | 0.2 | 0.2 | 0.2 |
| Enzymes e.g. Protease (84 mg/g active), Amylase (22 mg/g active) | 0.2 | 0.3 | 0.2 | 0.1 | 0.2 | 0.1 | 0.2 |
| Suds suppressor agglomerate (12.4 wt % active) | 0.2 | 0.2 | 0.2 | 0.2 | 0.2 | 0.2 | 0.2 |
| Sodium percarbonate (having from 12% to 15% active AvOx) | 7.2 | 7.1 | 4.9 | 5.4 | 6.9 | 19.3 | 13.1 |
| Additional Neat Perfume** | 0.5 | 0.5 | 0.5 | 0.5 | 0.5 | 0.5 | 0.5 |
| Amine* | 0.1 | 0.5 | 0.0 | 0.01 | 0.02 | 0.00 | 0.07 |
| Perfume Delivery System As Disclosed In The Present Specification Including Examples 2-4 | 0.05 | 0.0 | 0.1 | 0.0 | 0.2 | 0.4 | 0.0 |
| Perfume comprising one or more PRMs from Table 1 | 0.3 | 0.4 | 0.01 | 0.02 | 0.04 | 0.1 | 0.1 |
| Water | 1.4 | 1.4 | 1.4 | 1.4 | 1.4 | 1.4 | 1.4 |
| Misc | 0.1 | 0.1 | 0.1 | 0.1 | 0.1 | 0.1 | 0.1 |
| Total Parts | 100 | 100 | 100 | 100 | 100 | 100 | 100 |

*One or more materials comprising an amine moiety as disclosed in the present specification.
**Optional Example 7

Liquid Laundry Formulations (HDLs)

| Ingredient | HDL 1 | HDL 2 | HDL3 | HDL4 | HDL 5 | HDL 6 |
|---|---|---|---|---|---|---|
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |
| Ethoxysulfated hexamethylene diamine quaternized | 1.9 | 1.2 | 1.5 | 2.0 | 1.0 | 1.0 |
| Diethylene triamine penta methylene phosphonic acid | 0.3 | 0.2 | 0.2 | 0.3 | 0.1 | 0.2 |
| Enzymes | 1.20 | 0.80 | 0 | 1.2 | 0 | 0.8 |
| Brightener (disulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |

| Ingredient | HDL 1 | HDL 2 | HDL3 | HDL4 | HDL 5 | HDL 6 |
|---|---|---|---|---|---|---|
| Glutaraldehyde | 0 | 0 | 19 ppm | 0 | 13 ppm | 0 |
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Silicone (PDMS) emulsion | 0.003 | 0.003 | 0.003 | 0.003 | 0.003 | 0.003 |
| Additional Neat Perfume** | 0.7 | 0.5 | 0.8 | 0.8 | 0.6 | 0.6 |
| Amine* | 0.01 | 0.10 | 0.0 | 0.10 | 0.20 | 0.05 |
| Perfume comprising one or more PRMs from Table 1 | 0.02 | 0.15 | 0.0 | 0.2 | 0.3 | 0.1 |
| Perfume Delivery System As Disclosed In The Present Specification Including Examples 2-4 | 0.2 | 0.02 | 0.4 | 0.0 | 0.0 | 0.0 |
| Water | Balance | Balance | Balance | Balance | Balance | Balance |

*One or more materials comprising an amine moiety as disclosed in the present specification.
**Optional.

Example 8

Shampoo Formulations

| Ingredient | |
|---|---|
| Ammonium Laureth Sulfate (AE$_3$S) | 6.00 |
| Ammonium Lauryl Sulfate (ALS) | 10.00 |
| Laureth-4 Alcohol | 0.90 |
| Trihydroxystearin$^{(7)}$ | 0.10 |
| Perfume comprising one or more PRMs from Table 1 | 0.60 |
| Sodium Chloride | 0.40 |
| Citric Acid | 0.04 |
| Sodium Citrate | 0.40 |
| Sodium Benzoate | 0.25 |
| Ethylene Diamine Tetra Acetic Acid | 0.10 |
| Dimethicone$^{(9,10,11)}$ | 1.00$^{(9)}$ |
| Water and Minors (QS to 100%) | Balance |

Example 9

Fine Fragrance Formulations

| Ingredient | 1 | 2 | 3 |
|---|---|---|---|
| Cyclic oligosaccharide | 0 | 5 | 10 |
| Ethanol | 90 | 75 | 80 |
| Perfume comprising one or more PRMs from Table 1 | 10 | 20 | 10 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A consumer product comprising an adjunct ingredient and, based on total consumer product weight, from about 0.0001% to about 25% of one or more perfume raw materials selected from:
   a) 3a-isopropyl-2,6-dimethyl-octahydro-benzofuran; and stereoisomers of 3a-isopropyl-2,6-dimethyl-octahydro-benzofuran; and
   b) one or more optional perfume raw materials selected from; 4-(2,4-dimethyl-cyclohex-3-enylidene)-butan-2-one; 4-isopropyl-1,5-dimethyl-2-oxa-bicyclo[2.2.2]octane; 4-(1,2-dimethyl-propyl)-1-methyl-2-oxa-bicyclo[2.2.2]octane; 2-(3-methyl-butyl)-3-vinyl-cyclopentanone; 2,5,5-trimethyl-2-propyl-[1,3]dioxane; 1,2,4-trimethyl-bicyclo[2.2.1]heptane-2-carboxylic acid methyl ester; 8-ethoxy-2,6-dimethyl-nona-2,6-diene; 2,2,3a,7-tetramethyl-octahydro-benzofuran; 4-cyclopropylmethoxymethyl-5-methyl-cyclohexene; cyclopropanecarboxylic acid 1-methyl-hexyl ester; 3-isopropenyl-6-methyl-2-propenyl-tetrahydro-pyran; acetic acid 3-isopropyl-1,2-dimethyl-cyclopentyl ester; 1-(2,4,6-trimethyl-cyclohex-3-enyl)-propan-1-one; 2-(hex-3-enyl)-5-methyl-tetrahydro-furan; 3-sec-Butyl-1,5-dimethyl-2-oxa-bicyclo[2.2.2]octane; 1-(6-Isopropyl-2-methyl-cyclohex-3-enyl)-ethanone; 1-(6-Isopropyl-4-methyl-cyclohex-3-enyl)-ethanone; 4-(3-Methoxy-1-methyl-propyl)-1-methyl-cyclohexene; 3-(1,1-Dimethoxy-ethyl)-1,1-dimethyl-cyclohexane; 2,4-Dimethyl-2-(4-methyl-pent-3-nyl)-[1,3]dioxolane; and all stereoisomers of said one or more optional perfume raw materials.

2. A consumer product according to claim 1, said consumer product being a cleaning and/or treatment composition, said composition comprising, based on total composition weight, from about 0.0001% to about 25% of one or more perfume raw materials selected from:
 a) 3a-isopropyl-2,6-dimethyl-octahydro-benzofuran; and stereoisomers of 3a-isopropyl-2,6-dimethyl-octahydro-benzofuran; and
 b) one or more optional perfume raw materials selected from 4 (2,4-dimethyl-cyclohex-3-enylidene)-butan-2-one; 4-isopropyl-1,5-dimethyl-2-oxa-bicyclo[2.2.2]octane; 4-(1,2-dimethyl-propyl)-1-methyl-2-oxa-bicyclo[2.2.2]octane; 2-(3-methyl-butyl)-3-vinyl-cyclopentanone; 2,5,5-trimethyl-2-propyl-[1,3]dioxane; 1,2,4-trimethyl-bicyclo[2.2.1]heptane-2-carboxylic acid methyl ester; 8-ethoxy-2,6-dimethyl-nona-2,6-diene; 2,2,3a,7-tetramethyl-octahydro-benzofuran; 4-cyclopropylmethoxymethyl-5-methyl-cyclohexene; cyclopropanecarboxylic acid 1-methyl-hexyl ester; 3-isopropenyl-6-methyl-2-propenyl-tetrahydro-pyran; acetic acid 3-isopropyl-1,2-dimethyl-cyclopentyl ester; 1-(2,4,6-trimethyl-cyclohex-3-enyl)-propan-1-one; 2-(hex-3-enyl)-5-methyl-tetrahydro-furan; 3-sec-Butyl-1,5-dimethyl-2-oxa-bicyclo[2.2.2]octane; 1-(6-Isopropyl-2-methyl-cyclohex-3-enyl)-ethanone; 1-(6-Isopropyl-4-methyl-cyclohex-3-enyl)-ethanone; 4-(3-Methoxy-1-methyl-propyl)-1-methyl-cyclohexene; 3-(1,1-Dimethoxy-ethyl)-1,1-dimethyl-cyclohexane; 2,4-Dimethyl-2-(4-methyl-pent-3-nyl)-[1,3]dioxolane and all stereoisomers of said one or more optional perfume raw materials.

3. A consumer product according to claim 1, said consumer product being a fabric and/or hard surface cleaning and/or treatment composition, said composition comprising, based on total composition weight, from about 0.0001% to about 25% of one or more perfume raw materials selected from:
 a) 3a-isopropyl-2,6-dimethyl-octahydro-benzofuran; and stereoisomers of 3a-isopropyl-2,6-dimethyl-octahydro-benzofuran; and
 b) one or more optional perfume raw materials selected from, 4 (2,4-dimethyl-cyclohex-3-enylidene)-butan-2-one; 4-isopropyl-1,5-dimethyl-2-oxa-bicyclo[2.2.2]octane; 4-(1,2-dimethyl-propyl)-1-methyl-2-oxa-bicyclo[2.2.2]octane; 2-(3-ethyl-butyl)-3-vinyl-cyclopentanone; 2,5,5-trimethyl-2-propyl-[1,3]dioxane; 1,2,4-trimethyl-bicyclo[2.2.1]heptane-2-carboxylic acid methyl ester; 8-ethoxy-2,6-dimethyl-nona-2,6-diene; 2,2,3a,7-tetramethyl-octahydro-benzofuran; 4-cyclopropylmethoxymethyl-5-methyl-cyclohexene; cyclopropanecarboxylic acid 1-methyl-hexyl ester; 3-isopropenyl-6-methyl-2-propenyl-tetrahydro-pyran; acetic acid 3-isopropyl-1,2-dimethyl-cyclopentyl ester; 1-(2,4,6-trimethyl-cyclohex-3-enyl)-propan-1-one; 2-(hex-3-enyl)-5-methyl-tetrahydro-furan; 3-sec-Butyl-1,5-dimethyl-2-oxa-bicyclo[2.2.2]octane; 1-(6-Isopropyl-2-methyl-cyclohex-3-enyl)-ethanone; 1-(6-Isopropyl-4-methyl-cyclohex-3-enyl)-ethanone; 4-(3-Methoxy-1-methyl-propyl)-1-methyl-cyclohexene; 3-(1,1-Dimethoxy-ethyl)-1,1-dimethyl-cyclohexane; 2,4-Dimethyl-2-(4-methyl-pent-3-nyl)-[1,3]dioxolane and all stereoisomers of said one or more optional perfume raw materials.

4. A consumer product according to claim 1, said consumer product being a detergent, said detergent comprising, based on total detergent weight, from about 0.0001% to about 25% of one or more perfume raw materials selected from:
 a) 3a-isopropyl-2,6-dimethyl-octahydro-benzofuran; and stereoisomers of 3a-isopropyl-2,6-dimethyl-octahydro-benzofuran; and
 b) one or more optional perfume raw materials selected from 4 (2,4-dimethyl-cyclohex-3-enylidene)-butan-2-one; 4-isopropyl-1,5-dimethyl-2-oxa-bicyclo[2.2.2]octane; 4-(1,2-dimethyl-propyl)-1-methyl-2-oxa-bicyclo[2.2.2]octane; 2-(3-methyl-butyl)-3-vinyl-cyclopentanone; 2,5,5-trimethyl-2-propyl-[1,3]dioxane; 1,2,4-trimethyl-bicyclo[2.2.1]heptane-2-carboxylic acid methyl ester; 8-ethoxy-2,6-dimethyl-nona-2,6-diene; 2,2,3a,7-tetramethyl-octahydro-benzofuran; 4-cyclopropylmethoxymethyl-5-methyl-cyclohexene; cyclopropanecarboxylic acid 1-methyl-hexyl ester; 3-isopropenyl-6-methyl-2-propenyl-tetrahydro-pyran; acetic acid 3-isopropyl-1,2-dimethyl-cyclopentyl ester; 1-(2,4,6-trimethyl-cyclohex-3-enyl)-propan-1-one; 2-(hex-3-enyl)-5-methyl-tetrahydro-furan; 3-sec-Butyl-1,5-dimethyl-2-oxa-bicyclo[2.2.2]octane; 1-(6-Isopropyl-2-methyl-cyclohex-3-enyl)-ethanone; 1-(6-Isopropyl-4-methyl-cyclohex-3-enyl)-ethanone; 4-(3-Methoxy-1-methyl-propyl)-1-methyl-cyclohexene; 3-(1,1-Dimethoxy-ethyl)-1,1-dimethyl-cyclohexane; 2,4-Dimethyl-2-(4-methyl-pent-3-nyl)-[1,3]dioxolane and all stereoisomers of said one or more optional perfume raw materials.

5. A consumer product according to claim 1, said consumer product being a highly compacted consumer product, said highly compacted consumer product comprising, based on total highly compacted consumer product weight, from about 0.0001% to about 25% of one or more perfume raw materials selected from:
 a) 3a-isopropyl-2,6-dimethyl-octahydro-benzofuran; and stereoisomers of 3a-isopropyl-2,6-dimethyl-octahydro-benzofuran; and
 b) one or more optional perfume raw materials selected from 4 (2,4-dimethyl-cyclohex-3-enylidene)-butan-2-one; 4-isopropyl-1,5-dimethyl-2-oxa-bicyclo[2.2.2]octane; 4-(1,2-dimethyl-propyl)-1-methyl-2-oxa-bicyclo[2.2.2]octane; 2-(3-methyl-butyl)-3-vinyl-cyclopentanone; 2,5,5-trimethyl-2-propyl-[1,3]dioxane; 1,2,4-trimethyl-bicyclo[2.2.1]heptane-2-carboxylic acid methyl ester; 8-ethoxy-2,6-dimethyl-nona-2,6-diene; 2,2,3a,7-tetramethyl-octahydro-benzofuran; 4-cyclopropylmethoxymethyl-5-methyl-cyclohexene; cyclopropanecarboxylic acid 1-methyl-hexyl ester; 3-isopropenyl-6-methyl-2-propenyl-tetrahydro-pyran; acetic acid 3-isopropyl-1,2-dimethyl-cyclopentyl ester; 1-(2,4,6-trimethyl-cyclohex-3-enyl)-propan-1-one; 2-(hex-3-enyl)-5-methyl-tetrahydro-furan; 3-sec-Butyl-1,5-dimethyl-2-oxa-bicyclo[2.2.2]octane; 1-(6-Isopropyl-2-methyl-cyclohex-3-enyl)-ethanone; 1-(6-Isopropyl-4-methyl-cyclohex-3-enyl)-ethanone; 4-(3-Methoxy-1-methyl-propyl)-1-methyl-cyclohexene; 3-(1,1-Dimethoxy-ethyl)-1,1-dimethyl-cyclohexane; 2,4-Dimethyl-2-(4-methyl-pent-3-nyl)-[1,3]dioxolane and all stereoisomers of said one or more optional perfume raw materials.

6. A consumer product according to claim 5, said consumer product being a highly compacted detergent, said highly compacted detergent comprising one or more perfume raw materials selected from:

a) 3a-isopropyl-2,6-dimethyl-octahydro-benzofuran; and stereoisomers of 3a-isopropyl-2,6-dimethyl-octahydro-benzofuran; and
b) one or more optional perfume raw materials selected from 4 (2,4-dimethyl-cyclohex-3-enylidene)-butan-2-one; 4-isopropyl-1,5-dimethyl-2-oxa-bicyclo[2.2.2]octane; 4-(1,2-dimethyl-propyl)-1-methyl-2-oxa-bicyclo[2.2.2]octane; 2-(3-methyl-butyl)-3-vinyl-cyclopentanone; 2,5,5-trimethyl-2-propyl-[1,3]dioxane; 1,2,4-trimethyl-bicyclo[2.2.1]heptane-2-carboxylic acid methyl ester; 8-ethoxy-2,6-dimethyl-nona-2,6-diene; 2,2,3a,7-tetramethyl-octahydro-benzofuran; 4-cyclopropylmethoxymethyl-5-methyl-cyclohexene; cyclopropanecarboxylic acid 1-methyl-hexyl ester; 3-isopropenyl-6-methyl-2-propenyl-tetrahydro-pyran; acetic acid 3-isopropyl-1,2-dimethyl-cyclopentyl ester; 1-(2,4,6-trimethyl-cyclohex-3-enyl)-propan-1-one; 2-(hex-3-enyl)-5-methyl-tetrahydro-furan; 3-sec-Butyl-1,5-dimethyl-2-oxa-bicyclo[2.2.2]octane; 1-(6-Isopropyl-2-methyl-cyclohex-3-enyl)-ethanone; 1-(6-Isopropyl-4-methyl-cyclohex-3-enyl)-ethanone; 4-(3-Methoxy-1-methyl-propyl)-1-methyl-cyclohexene; 3-(1,1-Dimethoxy-ethyl)-1,1-dimethyl-cyclohexane; 2,4-Dimethyl-2-(4-methyl-pent-3-nyl)-[1,3]dioxolane.

7. A perfume delivery system comprising from about 0.001% to about 50% of one or more perfume raw materials selected from:
a) 3a-isopropyl-2,6-dimethyl-octahydro-benzofuran; and stereoisomers of 3a-isopropyl-2,6-dimethyl-octahydro-benzofuran; and
b) one or more optional perfume raw materials selected from, 4-(2,4-dimethyl-cyclohex-3-enylidene)-butan-2-one; 4-isopropyl-1,5-dimethyl-2-oxa-bicyclo[2.2.2]octane; 4-(1,2-dimethyl-propyl)-1-methyl-2-oxa-bicyclo[2.2.2]octane; 2-(3-methyl-butyl)-3-vinyl-cyclopentanone; 2,5,5-trimethyl-2-propyl-[1,3]dioxane; 1,2,4-trimethyl-bicyclo[2.2.1]heptane-2-carboxylic acid methyl ester; 8-ethoxy-2,6-dimethyl-nona-2,6-diene; 2,2,3a,7-tetramethyl-octahydro-benzofuran; 4-cyclopropylmethoxymethyl-5-methyl-cyclohexene; cyclopropanecarboxylic acid 1-methyl-hexyl ester; 3-isopropenyl-6-methyl-2-propenyl-tetrahydro-pyran; acetic acid 3-isopropyl-1,2-dimethyl-cyclopentyl ester; 1-(2,4,6-trimethyl-cyclohex-3-enyl)-propan-1-one; 2-(hex-3-enyl)-5-methyl-tetrahydro-furan; 3-sec-Butyl-1,5-dimethyl-2-oxa-bicyclo[2.2.2]octane; 1-(6-Isopropyl-2-methyl-cyclohex-3-enyl)-ethanone; 1-(6-Isopropyl-4-methyl-cyclohex-3-enyl)-ethanone; 4-(3-Methoxy-1-methyl-propyl)-1-methyl-cyclohexene; 3-(1,1-Dimethoxy-ethyl)-1,1-dimethyl-cyclohexane; 2,4-Dimethyl-2-(4-methyl-pent-3-nyl)-[1,3]dioxolane and all stereoisomers of said one or more optional perfume raw materials; wherein said perfume delivery system is selected from a polymer assisted delivery system; a molecule-assisted delivery system; a fiber-assisted delivery system; an amine assisted delivery system; a cyclodextrin delivery system; a starch encapsulated accord; an inorganic carrier delivery system; or a pro-perfume.

8. A perfume delivery system according to claim 7, said perfume delivery system being a nanocapsule or a microcapsule comprising, based on total nanocapsule or microcapsule weight, from about 0.1% to about 99% of one or more perfume raw materials selected from:
a) 3a-isopropyl-2,6-dimethyl-octahydro-benzofuran; and stereoisomers of 3a-isopropyl-2,6-dimethyl-octahydro-benzofuran; and
b) one or more optional perfume raw materials selected from 4-(2,4-dimethyl-cyclohex-3-enylidene)-butan-2-one; 4-isopropyl-1,5-dimethyl-2-oxa-bicyclo[2.2.2]octane; 4-(1,2-dimethyl-propyl)-1-methyl-2-oxa-bicyclo[2.2.2]octane; 2-(3-methyl-butyl)-3-vinyl-cyclopentanone; 2,5,5-trimethyl-2-propyl-[1,3]dioxane; 1,2,4-trimethyl-bicyclo[2.2.1]heptane-2-carboxylic acid methyl ester; 8-ethoxy-2,6-dimethyl-nona-2,6-diene; 2,2,3a,7-tetramethyl-octahydro-benzofuran; 4-cyclopropylmethoxymethyl-5-methyl-cyclohexene; cyclopropanecarboxylic acid 1-methyl-hexyl ester; 3-isopropenyl-6-methyl-2-propenyl-tetrahydro-pyran; acetic acid 3-isopropyl-1,2-dimethyl-cyclopentyl ester; 1-(2,4,6-trimethyl-cyclohex-3-enyl)-propan-1-one; 2-(hex-3-enyl)-5-methyl-tetrahydro-furan; 3-sec-Butyl-1,5-dimethyl-2-oxa-bicyclo[2.2.2]octane; 1-(6-Isopropyl-2-methyl-cyclohex-3-enyl)-ethanone; 1-(6-Isopropyl-4-methyl-cyclohex-3-enyl)-ethanone; 4-(3-Methoxy-1-methyl-propyl)-1-methyl-cyclohexene; 3-(1,1-Dimethoxy-ethyl)-1,1-dimethyl-cyclohexane; 2,4-Dimethyl-2-(4-methyl-pent-3-nyl)-[1,3]dioxolane and all stereoisomers of said one or more optional perfume raw materials.

9. The perfume delivery system of claim 8, said perfume delivery system comprising one or more perfume raw materials selected from:
a) 3a-isopropyl-2,6-dimethyl-octahydro-benzofuran; and stereoisomers of 3a-isopropyl-2,6-dimethyl-octahydro-benzofuran; and
b) one or more optional perfume raw materials selected from 4 (2,4-dimethyl-cyclohex-3-enylidene)-butan-2-one; 4-isopropyl-1,5-dimethyl-2-oxa-bicyclo[2.2.2]octane; 4-(1,2-dimethyl-propyl)-1-methyl-2-oxa-bicyclo[2.2.2]octane; 2-(3-methyl-butyl)-3-vinyl-cyclopentanone; 8-ethoxy-2,6-dimethyl-nona-2,6-diene; 2,2,3a,7-tetramethyl-octahydro-benzofuran; 4-cyclopropylmethoxymethyl-5-methyl-cyclohexene; cyclopropanecarboxylic acid 1-methyl-hexyl ester; 3-isopropenyl-6-methyl-2-propenyl-tetrahydro-pyran; acetic acid 3-isopropyl-1,2-dimethyl-cyclopentyl ester; 1-(2,4,6-trimethyl-cyclohex-3-enyl)-propan-1-one; 2-(hex-3-enyl)-5-methyl-tetrahydro-furan; 3-sec-Butyl-1,5-dimethyl-2-oxa-bicyclo[2.2.2]octane; 1-(6-Isopropyl-2-methyl-cyclohex-3-enyl)-ethanone; 1-(6-Isopropyl-4-methyl-cyclohex-3-enyl)-ethanone; 4-(3-Methoxy-1-methyl-propyl)-1-methyl-cyclohexene; 2,4-Dimethyl-2-(4-methyl-pent-3-nyl)-[1,3]dioxolane and all stereoisomers of said one or more optional perfume raw materials.

10. A perfume delivery system according to claim 8, said perfume delivery system being a starch encapsulated accord.

11. A perfume delivery system according to claim 7, said perfume delivery system being a cyclodextrin delivery system comprising, based on total cyclodextrin delivery system weight, from 0.1% to about 99% of one or more perfume raw materials selected from:
a) 3a-isopropyl-2,6-dimethyl-octahydro-benzofuran; and stereoisomers of 3a-isopropyl-2,6-dimethyl-octahydro-benzofuran; and
b) one or more optional perfume raw materials selected from 4 (2,4-dimethyl-cyclohex-3-enylidene)-butan-2-one; 4-isopropyl-1,5-dimethyl-2-oxa-bicyclo[2.2.2]octane; 4-(1,2-dimethyl-propyl)-1-methyl-2-oxa-bicyclo

[2.2.2]octane; 2-(3-methyl-butyl)-3-vinyl-cyclopentanone; 2,5,5-trimethyl-2-propyl-[1,3]dioxane; 1,2,4-trimethyl-bicyclo[2.2.1]heptane-2-carboxylic acid methyl ester; 8-ethoxy-2,6-dimethyl-nona-2,6-diene; 2,2,3a,7-tetramethyl-octahydro-benzofuran; 4-cyclopropylmethoxymethyl-5-methyl-cyclohexene; cyclopropanecarboxylic acid 1-methyl-hexyl ester; 3-isopropenyl-6-methyl-2-propenyl-tetrahydro-pyran; acetic acid 3-isopropyl-1,2-dimethyl-cyclopentyl ester; 1-(2,4,6-trimethyl-cyclohex-3-enyl)-propan-1-one; 2-(hex-3-enyl)-5-methyl-tetrahydro-furan; 3-sec-Butyl-1,5-dimethyl-2-oxa-bicyclo[2.2.2]octane; 1-(6-Isopropyl-2-methyl-cyclohex-3-enyl)-ethanone; 1-(6-Isopropyl-4-methyl-cyclohex-3-enyl)-ethanone; 4-(3-Methoxy-1-methyl-propyl)-1-methyl-cyclohexene; 3-(1,1-Dimethoxy-ethyl)-1,1-dimethyl-cyclohexane; 2,4-Dimethyl-2-(4-methyl-pent-3-nyl)-[1,3]dioxolane and all stereoisomers of said one or more optional perfume raw materials.

12. A perfume delivery system according to claim 7, said perfume delivery system being a polymer assisted delivery matrix system comprising, based on total polymer assisted delivery matrix system weight, from 0.1% to about 99% of one or more perfume raw materials selected from:
    a) 3a-isopropyl-2,6-dimethyl-octahydro-benzofuran; and stereoisomers of 3a-isopropyl-2,6-dimethyl-octahydro-benzofuran; and
    b) one or more optional perfume raw materials selected from 4 (2,4-dimethyl-cyclohex-3-enylidene)-butan-2-one; 4-isopropyl-1,5-dimethyl-2-oxa-bicyclo[2.2.2]octane; 4-(1,2-dimethyl-propyl)-1-methyl-2-oxa-bicyclo[2.2.2]octane; 2-(3-methyl-butyl)-3-vinyl-cyclopentanone; 2,5,5-trimethyl-2-propyl-[1,3]dioxane; 1,2,4-trimethyl-bicyclo[2.2.1]heptane-2-carboxylic acid methyl ester; 8-ethoxy-2,6-dimethyl-nona-2,6-diene; 2,2,3a,7-tetramethyl-octahydro-benzofuran; 4-cyclopropylmethoxymethyl-5-methyl-cyclohexene; cyclopropanecarboxylic acid 1-methyl-hexyl ester; 3-isopropenyl-6-methyl-2-propenyl-tetrahydro-pyran; acetic acid 3-isopropyl-1,2-dimethyl-cyclopentyl ester; 1-(2,4,6-trimethyl-cyclohex-3-enyl)-propan-1-one; 2-(hex-3-enyl)-5-methyl-tetrahydro-furan; 3-sec-Butyl-1,5-dimethyl-2-oxa-bicyclo[2.2.2]octane; 1-(6-Isopropyl-2-methyl-cyclohex-3-enyl)-ethanone; 1-(6-Isopropyl-4-methyl-cyclohex-3-enyl)-ethanone; 4-(3-Methoxy-1-methyl-propyl)-1-methyl-cyclohexene; 3-(1,1-Dimethoxy-ethyl)-1,1-dimethyl-cyclohexane; 2,4-Dimethyl-2-(4-methyl-pent-3-nyl)-[1,3]dioxolane and all stereoisomers of said one or more optional perfume raw materials.

13. A perfume delivery system according to claim 7, said perfume delivery system being an amine assisted delivery system, said amine assisted delivery system comprising, based on total amine assisted delivery system weight, from 1% to about 99% of one or more perfume raw materials selected from:
    a) 3a-isopropyl-2,6-dimethyl-octahydro-benzofuran; and stereoisomers of 3a-isopropyl-2,6-dimethyl-octahydro-benzofuran; and
    b) one or more optional perfume raw materials selected from 4-(2,4-dimethyl-cyclohex-3-enylidene)-butan-2-one; 4-isopropyl-1,5-dimethyl-2-oxa-bicyclo[2.2.2]octane; 4-(1,2-dimethyl-propyl)-1-methyl-2-oxa-bicyclo[2.2.2]octane; 2-(3-methyl-butyl)-3-vinyl-cyclopentanone; 2,5,5-trimethyl-2-propyl-[1,3]dioxane; 1,2,4-trimethyl-bicyclo[2.2.1]heptane-2-carboxylic acid methyl ester; 8-ethoxy-2,6-dimethyl-nona-2,6-diene; 2,2,3a,7-tetramethyl-octahydro-benzofuran; 4-cyclopropylmethoxymethyl-5-methyl-cyclohexene; cyclopropanecarboxylic acid 1-methyl-hexyl ester; 3-isopropenyl-6-methyl-2-propenyl-tetrahydro-pyran; acetic acid 3-isopropyl-1,2-dimethyl-cyclopentyl ester; 1-(2,4,6-trimethyl-cyclohex-3-enyl)-propan-1-one; 2-(hex-3-enyl)-5-methyl-tetrahydro-furan; 3-sec-Butyl-1,5-dimethyl-2-oxa-bicyclo[2.2.2]octane; 1-(6-Isopropyl-2-methyl-cyclohex-3-enyl)-ethanone; 1-(6-Isopropyl-4-methyl-cyclohex-3-enyl)-ethanone; 4-(3-Methoxy-1-methyl-propyl)-1-methyl-cyclohexene; 3-(1,1-Dimethoxy-ethyl)-1,1-dimethyl-cyclohexane; 2,4-Dimethyl-2-(4-methyl-pent-3-nyl)-[1,3]dioxolane and all stereoisomers of said one or more optional perfume raw materials.

14. A perfume delivery system according to claim 7, said perfume delivery system being a pro-perfume amine reaction product, said pro-perfume amine reaction product comprising, based on total pro-perfume amine reaction product weight, from 0.1% to about 99% of one or more perfume raw materials selected from:
    a) 3a-isopropyl-2,6-dimethyl-octahydro-benzofuran; and stereoisomers of 3a-isopropyl-2,6-dimethyl-octahydro-benzofuran; and
    b) one or more optional perfume raw materials selected from 4-(2,4-dimethyl-cyclohex-3-enylidene)-butan-2-one; 4-isopropyl-1,5-dimethyl-2-oxa-bicyclo[2.2.2]octane; 4-(1,2-dimethyl-propyl)-1-methyl-2-oxa-bicyclo[2.2.2]octane; 2-(3-methyl-butyl)-3-vinyl-cyclopentanone; 2,5,5-trimethyl-2-propyl-[1,3]dioxane; 1,2,4-trimethyl-bicyclo[2.2.1]heptane-2-carboxylic acid methyl ester; 8-ethoxy-2,6-dimethyl-nona-2,6-diene; 2,2,3a,7-tetramethyl-octahydro-benzofuran; 4-cyclopropylmethoxymethyl-5-methyl-cyclohexene; cyclopropanecarboxylic acid 1-methyl-hexyl ester; 3-isopropenyl-6-methyl-2-propenyl-tetrahydro-pyran; acetic acid 3-isopropyl-1,2-dimethyl-cyclopentyl ester; 1-(2,4,6-trimethyl-cyclohex-3-enyl)-propan-1-one; 2-(hex-3-enyl)-5-methyl-tetrahydro-furan; 3-sec-Butyl-1,5-dimethyl-2-oxa-bicyclo[2.2.2]octane; 1-(6-Isopropyl-2-methyl-cyclohex-3-enyl)-ethanone; 1-(6-Isopropyl-4-methyl-cyclohex-3-enyl)-ethanone; 4-(3-Methoxy-1-methyl-propyl)-1-methyl-cyclohexene; 3-(1,1-Dimethoxy-ethyl)-1,1-dimethyl-cyclohexane; 2,4-Dimethyl-2-(4-methyl-pent-3-nyl)-[1,3]dioxolane and all stereoisomers of said one or more optional perfume raw materials.

\* \* \* \* \*